(12) United States Patent
Ziebol et al.

(10) Patent No.: US 9,022,984 B2
(45) Date of Patent: May 5, 2015

(54) APPARATUS FOR DELIVERY OF DEVICE AND ANTIMICROBIAL AGENT INTO TRANS-DERMAL CATHETER

(75) Inventors: Robert J. Ziebol, Blaine, MN (US); William S. Nettekoven, Stillwater, MN (US); Mark A. Rydell, Golden Valley, MN (US)

(73) Assignee: Pursuit Vascular, Inc., Maple Grove, MN (US)

( * ) Notice: Subject to any disclaimer, the term of this patent is extended or adjusted under 35 U.S.C. 154(b) by 538 days.

(21) Appl. No.: 12/605,963

(22) Filed: Oct. 26, 2009

(65) Prior Publication Data

US 2010/0106102 A1    Apr. 29, 2010

Related U.S. Application Data

(60) Provisional application No. 61/108,716, filed on Oct. 27, 2008.

(51) Int. Cl.
*A61M 39/18* (2006.01)
*A61M 25/01* (2006.01)
(Continued)

(52) U.S. Cl.
CPC ............... *A61M 25/01* (2013.01); *A61M 39/18* (2013.01); *A61M 2025/0018* (2013.01);
(Continued)

(58) Field of Classification Search
CPC ................. A61M 25/0017; A61M 2025/0018; A61M 2025/0019; A61M 25/0111; A61M 39/165; A61M 39/18
USPC ........................... 604/159, 160, 161, 163, 192
See application file for complete search history.

(56) References Cited

U.S. PATENT DOCUMENTS 3,262,448 A  *  7/1966  Ring et al. .................... 604/159
3,595,241 A       7/1971  Sheridan
(Continued)

FOREIGN PATENT DOCUMENTS

| CN | 102202716 | 9/2011 |
|----|-----------|--------|
| EP | 1442753   | 2/2007 |

(Continued)

OTHER PUBLICATIONS

PCT International Search Report and Written Opinion from corresponding International Application No. PCT/US2009/062190, mailed May 26, 2010, 11 pages.

(Continued)

*Primary Examiner* — Bhisma Mehta
*Assistant Examiner* — Larry R Wilson
(74) *Attorney, Agent, or Firm* — Pauly, Devries, Smith & Deffner, LLC

(57) ABSTRACT

An apparatus for delivery of an elongate member into the lumen of a trans-dermal catheter. In a preferred embodiment, the apparatus comprises a protective sheath configured to at least substantially surround an elongate member; and slidable member configured to travel along the protective sheath, the slidable member operatively coupled to the elongate member; wherein the elongate member is insertable into a lumen of a trans-dermal catheter by moving the slidable member along at least a part of the length of the protective sheath. In another embodiment, the apparatus comprises a protective sheath configured to at least substantially surround an elongate member; a slidable member configured to travel along the protective sheath, the slidable member operatively coupled to the elongate member; and a connecting member positioned on the distal end of the protective sheath, the connecting member configured to lock onto the distal end of a trans-dermal catheter; wherein the elongate member is insertable into the lumen of the trans-dermal catheter by moving the slidable member along at least a part of the length of the protective sheath.

24 Claims, 17 Drawing Sheets

(51) Int. Cl.
*A61M 39/16* (2006.01)
*A61L 2/18* (2006.01)
*A61M 25/00* (2006.01)
*A61M 5/00* (2006.01)

(52) U.S. Cl.
CPC .... *A61M 2025/0019* (2013.01); *A61M 39/165* (2013.01); *A61M 25/0111* (2013.01); *A61M 25/0017* (2013.01); *A61L 2/186* (2013.01); *A61L 2202/24* (2013.01); *A61M 5/001* (2013.01); *A61M 25/0105* (2013.01); *A61M 2025/0056* (2013.01); *A61M 2209/10* (2013.01)

(56) References Cited

U.S. PATENT DOCUMENTS

| | | |
|---|---|---|
| 4,331,783 A | 5/1982 | Stoy |
| 4,337,327 A | 6/1982 | Stoy |
| 4,369,294 A | 1/1983 | Stoy |
| 4,370,451 A | 1/1983 | Stoy |
| 4,379,874 A | 4/1983 | Stoy |
| 4,420,589 A | 12/1983 | Stoy |
| 4,446,967 A | 5/1984 | Halkyard |
| 4,631,188 A | 12/1986 | Stoy et al. |
| 4,705,790 A | 11/1987 | Hubele et al. |
| 4,769,013 A | 9/1988 | Lorenz et al. |
| 4,808,158 A | 2/1989 | Kreuzer et al. |
| 4,894,056 A | 1/1990 | Bommarito |
| 5,015,238 A | 5/1991 | Solomon et al. |
| 5,071,413 A | 12/1991 | Utterberg et al. |
| 5,154,920 A | 10/1992 | Flesher et al. |
| 5,240,675 A | 8/1993 | Wilk et al. |
| 5,297,310 A | 3/1994 | Cox et al. |
| 5,337,730 A | 8/1994 | Maguire |
| 5,366,505 A | 11/1994 | Farber |
| 5,370,640 A | 12/1994 | Kolff |
| 5,375,589 A | 12/1994 | Bhatta |
| 5,407,807 A | 4/1995 | Markus |
| 5,409,012 A | 4/1995 | Sahatjian |
| 5,628,733 A | 5/1997 | Zinreich et al. |
| 5,782,808 A | 7/1998 | Folden |
| 5,902,631 A | 5/1999 | Wang et al. |
| 6,045,623 A | 4/2000 | Cannon |
| 6,059,107 A | 5/2000 | Nøsted et al. |
| 6,183,450 B1 | 2/2001 | Lois |
| 6,232,406 B1 | 5/2001 | Stoy |
| 6,409,716 B1 | 6/2002 | Sahatjian et al. |
| 6,444,318 B1 | 9/2002 | Guire et al. |
| 6,605,294 B2 | 8/2003 | Sawhney |
| 6,605,751 B1 | 8/2003 | Gibbins et al. |
| 6,634,498 B2 | 10/2003 | Kayerød et al. |
| 6,725,492 B2 | 4/2004 | Moore et al. |
| 7,097,850 B2 | 8/2006 | Chappa et al. |
| 7,195,615 B2 | 3/2007 | Tan |
| 7,442,402 B2 | 10/2008 | Chudzik et al. |
| 8,500,717 B2 | 8/2013 | Becker |
| 8,622,995 B2 | 1/2014 | Ziebol et al. |
| 8,622,996 B2 | 1/2014 | Ziebol et al. |
| 2004/0034329 A1 | 2/2004 | Mankus et al. |
| 2004/0156908 A1 | 8/2004 | Polaschegg |
| 2005/0124970 A1 | 6/2005 | Kunin et al. |
| 2005/0171493 A1 | 8/2005 | Nicholls |
| 2005/0220882 A1 | 10/2005 | Pritchard |
| 2005/0267421 A1 | 12/2005 | Wing |
| 2005/0288551 A1 | 12/2005 | Callister |
| 2006/0024372 A1 | 2/2006 | Utterberg et al. |
| 2006/0206178 A1 | 9/2006 | Kim |
| 2008/0132880 A1 | 6/2008 | Buchman |
| 2008/0319423 A1 | 12/2008 | Tanghoj et al. |
| 2009/0062766 A1 | 3/2009 | Howlett et al. |
| 2009/0247485 A1 | 10/2009 | Ahmed et al. |
| 2010/0106103 A1 | 4/2010 | Ziebol et al. |
| 2013/0144258 A1 | 6/2013 | Ziebol et al. |
| 2013/0184679 A1 | 7/2013 | Ziebol et al. |
| 2013/0204231 A1 | 8/2013 | Ziebol et al. |
| 2013/0274686 A1 | 10/2013 | Ziebol et al. |

FOREIGN PATENT DOCUMENTS

| | | |
|---|---|---|
| EP | 1813293 | 8/2007 |
| WO | 2006102756 | 10/2006 |
| WO | 2010062589 | 6/2010 |
| WO | 2013009998 | 1/2013 |

OTHER PUBLICATIONS

Non-Final Office Action, mailed Feb. 17, 2012 in co-pending U.S. Appl. No. 12/605,966, "Device for Delivery of Antimicrobial Agent Into Trans-Dermal Catheter," 11 pages.

Response (submitted Jun. 18, 2012) to Non-Final Office Action mailed Feb. 17, 2012 in co-pending U.S. Appl. No. 12/605,966, "Device for Delivery of Antimicrobial Agent Into Trans-Dermal Catheter," 12 pages.

PCT Notification Concerning Transmittal of International Preliminary Report on Patentability, mailed May 12, 2011, from International Application No. PCT/US2009/062190, corresponding to U.S. Appl. No. 61/108,716, 6 pages.

Non-Final Office Action from U.S. Appl. No. 13/752,385, mailed Jun. 12, 2013, 25 pages.

Non-Final Office Action from U.S. Appl. No. 13/834,755, mailed Jun. 20, 2013, 30 pages.

Non Final Office Action for U.S. Appl. No. 12/605,966, mailed Oct. 2, 2014 (23 pages).

Non-Final Office Action for U.S. Appl. No. 13/915,605, mailed Sep. 25, 2014 (15 pages).

Response to Communication Pursuant to Article 94(3) EPC for European Patent Application No. 098295876, mailed Nov. 29, 2012 and filed with the EPO Mar. 18, 2013 (7 pages).

Final Office Action for U.S. Appl. No. 13/915,605, mailed Dec. 27, 2013 (14 pages).

Amendment and Response After Final submitted on Feb. 27, 2014 for U.S. Appl. No. 13/915,605, (12 pages).

International Preliminary Report on Patentability for PCT/US2012/046496, mailed Jan. 23, 2014 (8 pages).

Notice of Allowance for U.S. Appl. No. 13/752,385, mailed Nov. 22, 2013 (12 pages).

Notice of Allowance for U.S. Appl. No. 13/834,755, mailed Nov. 22, 2013 (12 pages).

Final Office Action, mailed Oct. 18, 2012 in U.S. Appl. No. 12/605,966, "Device for Delivery of Antimicrobial Agent Into Trans-Dermal Catheter," (14 pages).

International Search Report and Written Opinion, for PCT/US2012/046496, mailed Jan. 28, 2013, (12 pages).

Notification of First Office Action, mailed Dec. 4, 2012, from Chinese Application No. 200980142920.4, based on PCT/US2009/062190 and U.S. Appl. No. 61/108,716, 9 pages.

Response to Non-Final Office Action, mailed Feb. 17, 2012, in co-pending U.S. Appl. No. 12/605,966, filed with USPTO Jun. 18, 2012 (12 pages).

Response to Final Office Action, mailed Oct. 18, 2012, in co-pending U.S. Appl. No. 12/605,966, filed with USPTO Dec. 5, 2012 (6 pages).

Non-Final Office Action from U.S. Appl. No. 13/915,605, mailed Aug. 29, 2013, 20 pages.

* cited by examiner

SECTION A-A

SECTION B-B

SECTION C-C

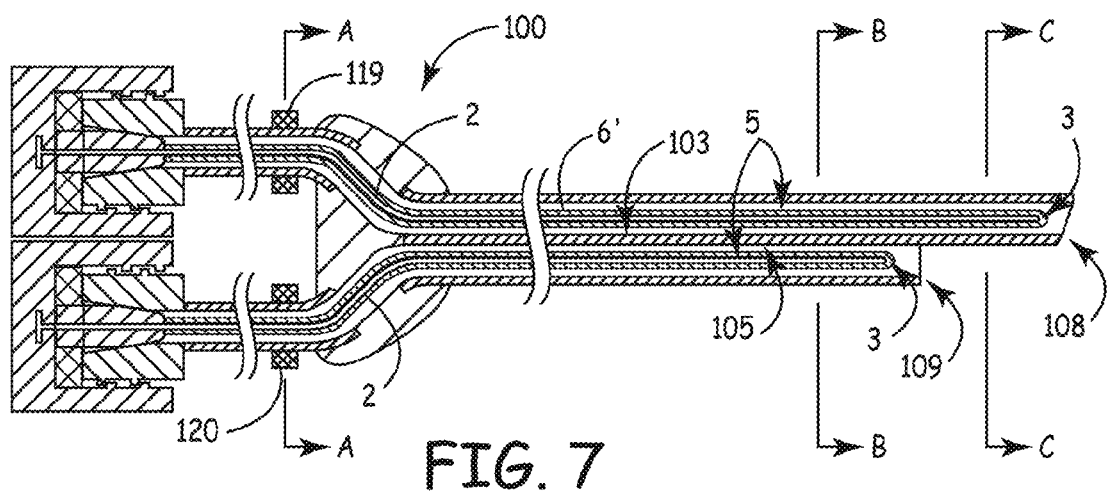
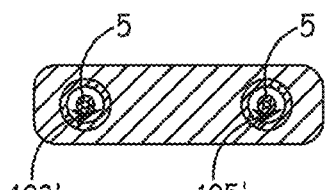
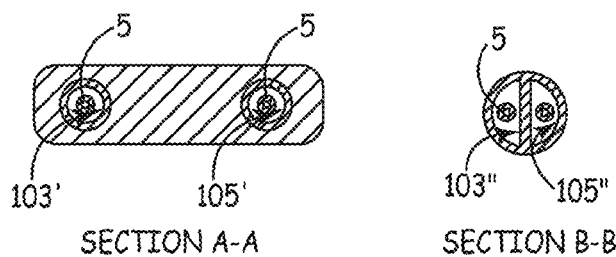
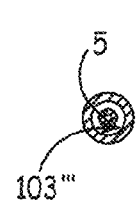
SECTION A-A
FIG. 7A
SECTION B-B
FIG. 7B
SECTION C-C
FIG. 7C

SECTION B-B

SECTION C-C

APPARATUS FOR DELIVERY OF DEVICE AND ANTIMICROBIAL AGENT INTO TRANS-DERMAL CATHETER

This application claims the benefit of U.S. Provisional Application No. 61/108,716, filed Oct. 27, 2008, the content of which is herein incorporated by reference in its entirety.

FIELD OF THE INVENTION

The invention relates to medical devices for treating and preventing infectious organisms, and more particularly, to systems for delivering antimicrobial agents into the lumen of catheters and drainage tubes.

BACKGROUND OF THE INVENTION

Contamination of medical devices, such as catheters and drainage tubes, by infectious organisms is a significant issue in the medical community. Hemodialysis catheters allow patients with renal disease to have toxins removed from their bloodstream. Without the use of catheters, many of these patients would not survive. However, long-term hemodialysis catheters have a serious drawback in that a significant percentage of catheters fail due to infection, resulting in elevated mortality rates and large annual healthcare costs associated with treatment. Furthermore, bloodstream infections are a leading cause of death in the United States, and many of those infections are attributable to vascular access devices. The mortality rate associated with such infections is considerable.

Infectious organisms typically colonize a catheter in three distinct ways. First, the infectious organisms may colonize the catheter by traveling in the bloodstream and eventually adhering to the catheter. This form of transmission is believed to be rare. Second, the infectious organisms may colonize the catheter by traveling along the outer wall of the catheter after entering at the catheter's body exit site. This method of infection transmission has been greatly reduced by tunneling the catheter under the skin for several centimeters, and by the addition of a cuff on the outer wall of the catheter. Body tissue grows into the cuff and creates a barrier for infection. Third, the infectious organisms may colonize the inner lumen of the catheter, entering at the hub and/or adaptor of the catheter, eventually migrating down the lumen of the catheter to the bloodstream. This method of infection transmission is a leading cause of bloodstream infections in patients with long-term indwelling catheters. Therefore, a need exists for improved devices, systems, and methods for eliminating, treating, and preventing such contamination.

The present invention prevents, reduces and can even eliminate infectious organisms within the inner luminal surface of a catheter or other similar medical devices by providing a means for the prolonged presence of an antimicrobial agent and/or providing a means for periodically scrubbing the lumen of the catheter or other medical device to remove the biofilm in which infectious organisms proliferate.

SUMMARY OF THE INVENTION

The present invention relates to devices, systems, and methods for treating, preventing and eliminating infectious organisms in medical devices, such as catheters and drainage tubes, and preventing the organisms from entering the bloodstream by delivering antimicrobial agents into the lumen of catheters and drainage tubes.

An embodiment of the invention, herein referred to as "the Device", is an elongate member that can be inserted into a medical device, such as a catheter or a drainage tube, for the prevention and treatment of infectious organisms within the medical device and in proximity to the elongate member, and further prevents the migration of infectious organisms into the body by providing a physical barrier. For the sake of simplicity, the term "catheter" is used for all medical devices in which the present invention can be inserted and used to treat, prevent, and eliminate infectious organisms.

An example embodiment includes an elongated and radially expandable plug comprising a suitable material into which an antimicrobial agent has been incorporated. The term "antimicrobial," as used here, includes any substance or substances that kills or inhibits the growth of microorganisms such as bacteria, fungi, protozoa, viruses, etc. It should also be noted that there can be one or more antimicrobial agents used. Therefore, throughout this document, antimicrobial agent refers to one or more antimicrobial agents. While the invention may be used in a variety of medical devices, a catheter, and more specifically a long-term hemodialysis catheter, will be used to describe the use of the invention. The use of these examples is not meant to confine or limit the use of the invention in other types of catheters or medical devices, such as peritoneal dialysis catheters, urinary catheters, PICC lines, feeding tubes and drainage catheters.

The present invention prevents and treats infectious organisms in the lumen of in-dwelling medical devices, such as long-term, trans-dermal catheters. The invention also prevents the formation of thrombus within the lumen of indwelling catheters by physically blocking blood from entering the catheter in the proximity of the Device, and, in some embodiments, by the incorporation of an antithrombotic agent.

One useful application of the invention is in preventing infections in people with hemodialysis catheters. The present invention prevents or eliminates infectious organisms on the luminal wall of a catheter by providing a means for the prolonged presence of an antimicrobial agent and/or providing a means for periodically scrubbing the luminal wall of the catheter to remove the biofilm in which infectious organisms proliferate.

Competing methods for preventing, eliminating, and treating infectious organisms in the lumen of a catheter are in limited use. One method uses an antimicrobial coating on or in the internal wall of the catheter. The issues that have precluded widespread use include the antimicrobial coating eventually wearing off, losing potency, or becoming covered with blood products, rendering the coating ineffective. When antibiotics are used as the antimicrobial agent, there is an additional concern regarding the emergence of resistant organisms to antibiotics and the risk of anaphylaxis to the antibiotics. Another method for treating infectious organisms in the lumen is the use of an antibiotic or antimicrobial liquid, known as a locking agent or locking solution. In this method, an antimicrobial fluid is injected into the catheter, and a cap is attached to the hub of the catheter to prevent the fluid from leaking out of the catheter and to prevent infectious organisms from entering into the lumen.

One issue precluding widespread use of this method is concern for the emergence of resistant organisms if an antibiotic agent is used. This concern may be virtually eliminated, however, by using a non-antibiotic antimicrobial. Another issue when dialysis catheters are filled with locking solutions is that the locking solution spills into the bloodstream. This occurs for two reasons. First, when the catheter is filled with a volume equal to the catheter volume, a significant portion of the fluid leaks out due to the nature of the laminar flow profile in the catheter. Second, blood flow by the tip/distal end results in the injected catheter locking solution being pulled out due to the Venturi effect, and density differences between the lock solution result in spillage of the solution into the bloodstream. It has been reported that 60% or more of the locking solution is spilled into the bloodstream in the first few hours after instillation. Accidental overdosing, either from injecting too much volume or too high of concentration of the locking solution, can cause additional spillage into the bloodstream. Spillage has resulted in adverse events, including death. For instance, spillage has resulted in death from transient hypocalcemia when a citrate solution was used. In addition, other adverse events may occur as some types of locking solutions may build up in the body.

In the case of using the Device with dialysis catheters, the present invention is designed to be replaced regularly after each dialysis session, approximately three times per week. This replenishes the antimicrobial agent with each replacement, resulting in a consistent and high concentration of antimicrobial agent present within the catheter on an ongoing basis resulting in decreased risk of infection.

In addition, separation between the antimicrobial agent and blood can result in lower infection rate, fewer side effects, and less risk of developing resistant bacteria because a non-antibiotic antimicrobial is used. In certain embodiments, the present invention creates a physical barrier between the blood and the antimicrobial agent. The barrier greatly reduces the exchange of antimicrobial agent with blood circulating in the body, resulting in fewer side effects from the antimicrobial agent. This can result in a more consistent level of antimicrobial agent along the length of the catheter adjacent to the Device. Additionally, the barrier reduces the amount of antimicrobial agent entering the bloodstream, thus reducing the risk of an adverse reaction to the agent or developing organisms resistant to the antimicrobial agent. In comparison, it is well-known that liquid locking agents can and do migrate into the bloodstream, and the blood can migrate into the catheter, thus reducing the effectiveness of the antimicrobial agent, increasing the possibility of bacteria entering the bloodstream and increasing the rate of thrombosis in the catheter. The act of flushing the catheter lumen with a fluid agent and/or inserting a plug into the lumen will result in the removal of blood from the lumen and thus reduce the risk of thrombosis. If the liquid agent is an anti-thrombotic lock, such as heparinized saline, the risk of thrombosis is further reduced. The use of a plug, as described in the present invention, prevents the blood from reentering the lumen and results in a lower risk of thrombosis in the lumen.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which:

FIG. 7 is a side cross-sectional view of two minimally hydrated plugs in each of the catheter lumens.

FIG. 7A is a cross-sectional view of minimally hydrated hydrogel plugs and the catheter taken along line A-A.

FIG. 7B is a cross-sectional view of the minimally hydrated hydrogel plugs and the catheter taken along line B-B.

FIG. 7C is a cross-sectional view of the minimally hydrated hydrogel plugs and the catheter taken along line C-C.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The following detailed description of example embodiments presents a description of certain specific embodiments to assist in understanding the claims. However, one may practice the present invention in a multitude of different embodiments as defined and covered by the claims.

Elongate Member for Insertion into a Catheter

In an example embodiment, the invention is a system for delivering an antimicrobial agent into the lumen of a trans-dermal catheter, the system comprising: an elongate member configured for insertion into a lumen of a catheter; an expandable portion of the elongate member, said expandable portion configured to increase in diameter upon exposure to an aqueous fluid; and an antimicrobial composition positioned to be delivered into the catheter.

Figure 1:
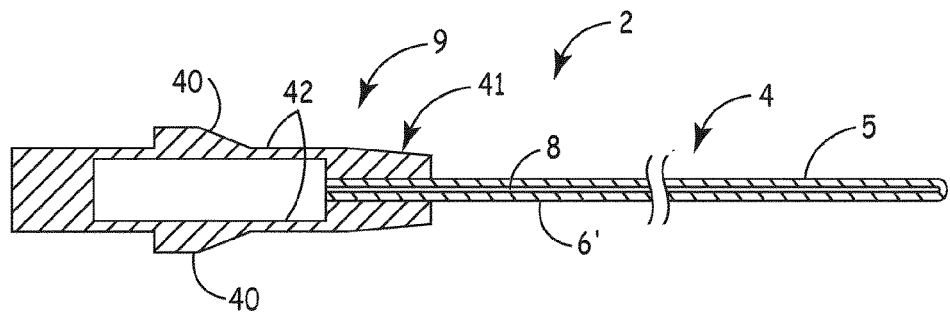
FIG. 1 is a side cross-sectional view of a hydrogel plug in its minimally hydrated state. The plug is shown in its preferred embodiment with a reinforcement member.

Referring now to the figures, example implementations of the invention are shown. Referring to FIG. 1, the elongate member 2 (also referred to as a plug) of the present invention can be configured to conform to at least a portion of the inner walls of a medical device. In the case of a catheter, the shape of the inner lumen wall typically changes over its length. The elongate member 2 can have, for example, the general shape of an elongated cylinder. In the case of a hemodialysis catheter, the plug generally matches the length and diameter of the lumen, such as approximately 45 cm long and 1-3 mm diameter, or it may be substantially shorter, passing just beyond the catheter adaptor where infectious organisms typically originate. The elongate member 2 can be made of a compliant material such as a sponge, a balloon, or a polymer.

In an example embodiment, the elongate member 2 comprises hydrogel. In one embodiment, at least a portion of the hydrogel expands upon insertion of the elongate member 2 into a catheter. The hydrogel may display non-uniform expansion upon exposure to an aqueous fluid. In yet another embodiment, the hydrogel may display anisotropic expansion upon exposure to an aqueous fluid. The compliance of the elongate member provides the advantage of ensuring a good seal with the catheter wall to minimize mixing of the antimicrobial agent and the blood.

In one embodiment, the invention comprises an elongate member 2 (see FIG. 1) configured for insertion into a lumen of a trans-dermal catheter 100 (see FIG. 6), said elongate member comprising a hydrogel; and an antimicrobial composition positioned to be delivered into the catheter, wherein the elongate member creates a contained volume of liquid within the lumen of the catheter.

To minimize the risk of pushing any preexisting biofilm and infectious organisms into the bloodstream, it is advantageous to have the elongate member be a smaller diameter than the catheter upon insertion. However, it is also desirable to have the elongate member be the same or larger diameter of the catheter while in use and upon removal such that the elongate member contacts the wall of the catheter.

The elongate member 2 may extend the entire length of the catheter 100 or, as described below in regard to the balloon and the polymer plug embodiments, it may reside only in a portion of the catheter. In addition, as described above, it may be substantially shorter than the catheter, passing just beyond the catheter adaptor where infectious organisms typically originate.

FIG. 1 shows one embodiment of a elongate member 2 formed with a hydrogel in its minimally hydrated state. The water content of the minimally hydrated hydrogel 6' is optionally set to achieve optimal flexibility, pushability, and a small diameter. A preferred embodiment has approximately 7% water content in a poly(acrylonitrile-co-acrylamide). The elongate member 2 includes a body 4 attached to a connector insert 9.

The connector insert 9 of FIG. 1 has a taper 41, connector insert protrusions 40, and flexible member 42. The connector insert 9 may be affixed to a hydrogel body 4 of sufficient length. It should be noted that while FIG. 1 shows the hydrogel body 4 as rod-shaped, it need not have such a shape; it need only be a substantially elongated member configured to be inserted into a tube/catheter. The connector insert 9 has a hole, approximately in the center and running axially along the distal end, wherein the hydrogel body 4 is passed and affixed to it. Another hole is elongated in shape and runs transversely through the connector insert 9. Flanking the elongated transverse hole are two flexible members 42 with protrusions 40 for locking the connector insert 9 into a mating connector with corresponding holes.

Figure 2:
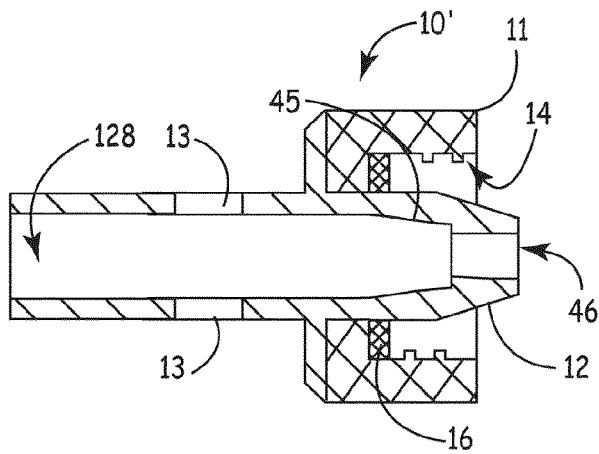
FIG. 2 is a side cross-sectional view of a modified male Luer connector.

In preferred embodiments, the invention comprises a connector at the proximal end of the elongate member 2 to create a liquid-tight and infection-tight seal at the hub of the catheter. The connector of the plug is optionally a Luer-Lock® connector or a modified Luer connector. FIG. 2 shows a modified male Luer connector 10' with locking ring 11, contamination barrier 16, male Luer taper 12, and modified male Luer connector cutouts 13. The modified male Luer connector insert hole 128 is sized to accommodate the connector insert 9. The modified male Luer connector 10' and locking ring 11 are used for connecting to the female Luer connector on the hemodialysis catheter. The modified male Luer connector 10' contains a hole 46 running the length of the connector through which the hydrogel body 4 can pass. Two substantially rectangular cutouts 13 are present in the wall of the connector 10' into which the protrusions 40 from the connector insert 9 fit and lock it into place. The connector 10 also incorporates one or more grooves that mate with the alignment protrusion 39, shown in FIG. 13A, of the connector insert 9 and whose proximal ends are wider and then tapered for orientation of the connector insert 9 to the Luer connector 10'.

In some embodiments, the connector contains an additional contamination barrier 16 that abuts the catheter connector on the most proximate surface. The purpose of the contamination barrier 16 is to prevent any infectious organisms from entering into the inside of the connector of the catheter. An alternative and/or additional location for the contamination barrier 16 is in the thread region of the connectors. In some embodiments, the connector contamination barrier 16 contains an antimicrobial material such as silver oxide or other antimicrobial agent.

Figure 3:
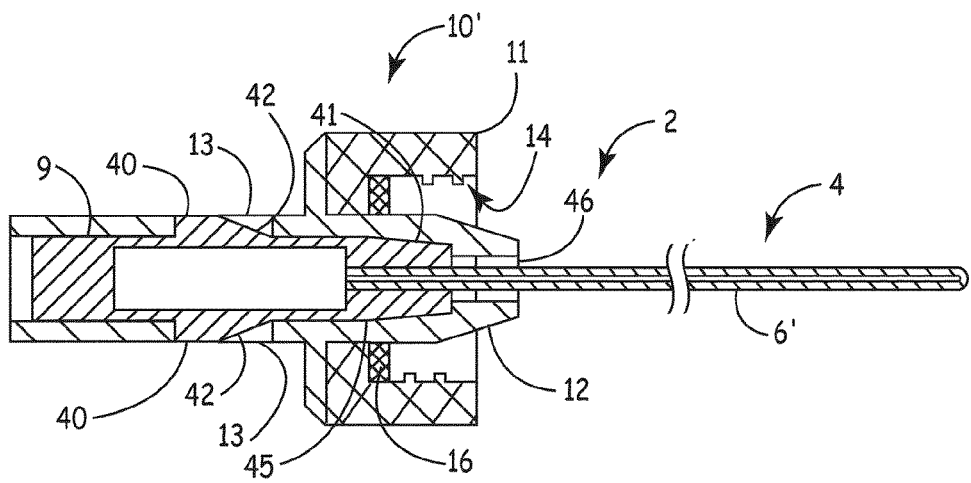
FIG. 3 is a side cross-sectional view of a hydrogel plug in its minimally hydrated state deployed through and locked into a modified male Luer connector. The plug is shown with a reinforcement member.

FIG. 3 shows one embodiment of the hydrogel plug 2 in its minimally hydrated state and locked into the modified male Luer connector 10' via connector insert protrusions 40. The modified male Luer connector 10' has a locking ring 11 with locking threads 14, an external male Luer taper 12, an internal female taper 45, through hole 46, and contamination barrier 16. As the connector insert 9 is inserted into the modified male Luer connector 10', the hydrogel body 4 passes through the modified male Luer connector 10' through hole 46, and the connector insert protrusions 40 deflect via the flexible members 42 and lock into the modified male Luer connector 10' via modified male Luer connector cutouts 13.

Figure 4:
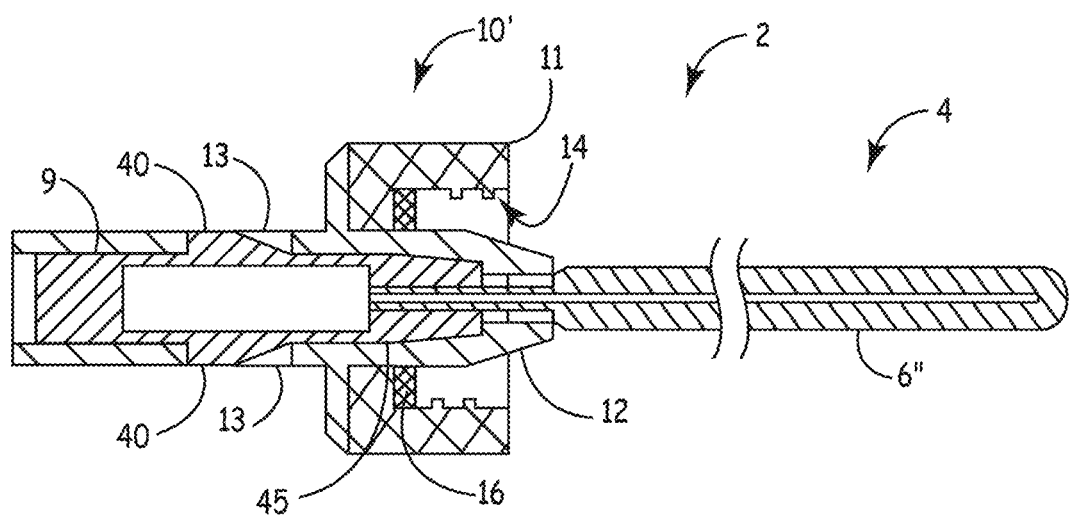
FIG. 4 is a side cross-sectional view of the hydrogel plug in its fully hydrated state deployed through and locked into a modified male Luer connector. The hydrogel plug is shown with a reinforcement member.

FIG. 4 shows the hydrogel plug 2 and hydrogel 6" in its fully hydrated state and locked into the modified male Luer connector 10' via the connector insert protrusions 40. In comparison to the minimally hydrated hydrogel 6', shown in FIGS. 1 and 3, the fully hydrated hydrogel 6" is significantly larger in diameter due to swelling and/or expansion. The amount of swelling or expanding can more than double the diameter of the hydrogel body 4. The swelling or expanding, as will be described in more detail later, is caused by absorption of fluid. The reinforcement member 8 shown in FIGS. 1 and 3 continues to remain internal to the hydrogel approximately along the central axis after swelling is complete.

In one embodiment of the present invention, the hydrogel used is a xerogel, a solid that changes size and stiffness as its hydration level varies. The hydrogel is a chemically or physically crosslinked polymer that is insoluble in water but swells to some equilibrium water content. Such hydrogels are relatively small, hard, and inflexible when fully dehydrated. As the hydrogel is hydrated, it becomes larger, softer and more flexible. It is preferable that the equilibrium water content is 25-99% by weight and more preferably 50-95% by weight and most preferably 70-91% by weight. The water content may be substantially less than that stated above, but the benefits of swelling will be diminished. The unique swellable properties of hydrogel are advantageous to the plug design. In some embodiments, the hydrogel swells or expands anisotropically, such that the hydrogel swells in diameter, but does not swell substantially in length. In practice, the hydrogel can swell more than 200% in diameter, but less than 5% in length. In another embodiment, the plug may comprise a substrate on which hydrogel is bonded.

Before the hydrogel is inserted into the catheter lumen, the lumen may be flushed with a fluid, such as saline, heparinized-saline, or a liquid antimicrobial agent to remove blood from the lumen. Initially, for insertion, the hydrogel body 4 has a low hydration level, causing the body 4 to initially be narrow and stiff enough to be easily pushed into the catheter lumen. The relatively narrow diameter minimizes the risk of transferring infectious organisms down the catheter as the plug 2 is advanced. Over time, the hydrogel body 4 absorbs the fluid that is present in the lumen, causing the body 4 to swell or expand. In a preferred embodiment, the hydrogel plug 2 may be inserted while its diameter is small. After insertion the body 4 increases in size and conforms to the catheter wall. In one embodiment, swell time for the plug to contact the Device wall is preferably between 0 minutes and 6 hours, optionally between 1 minute and 30 minutes, and alternatively between 1 minute and 10 minutes.

It can be desirable to have the elongate member 2 be flexible enough so it does not apply excessive straightening forces on the catheter. However, at the same time, the elongate member 2 should generally have enough column strength to allow the Device to be fully advanced into the catheter. The shaft, or body 4 of the elongate member, or plug 2 (the material running the length of the Device), may consist of a hollow space (generally running along the length of the Device) that is designed to accept a core, or reinforcement member 8, such as a wire. The core, or reinforcement member 8, is inserted into the hollow space to aid in pushing the Device into a catheter. In one embodiment, after the elongate member 2 is inserted into a catheter, the core, or reinforcement member 8, may be removed to eliminate the straightening forces of the reinforcement member 8. It is desirable in some embodiments to configure a hollow space in the shaft to be used as a conduit for antimicrobial fluid. The fluid can be injected at the proximal end and dispersed into the catheter lumen via the hollow space. In addition, an alternative embodiment may coat a filament or reinforcement member 8 comprised of a material that absorbs and subsequently releases an antimicrobial agent.

It is preferred to provide a means to strengthen the hydrogel rod. This is especially true in cases where hydrogel materials absorb substantial amounts of fluid that may weaken the material. The core, or reinforcement member 8, provides additional strength to the hydrogel body 4 to prevent fragmentation and prevents axial lengthening of the fully hydrated hydrogel body 6". In a preferred embodiment, the core, or reinforcement member 8, has a tensile breaking strength of at least 4.4 newtons.

Depending on its application and how the hydrogel is to be used, the core, or reinforcing member 8, can be either of similar elongation properties (the inverse of Young's modulus), such as a polyurethane material, or it can be of substantially lower elongation properties, such as a polyester material. If the swelling of the hydrogel is in a confined space which applies a substantially high normal force to the surface, it may be desirable to have the incorporated elongation of the core, or reinforcement member 8, be substantially equivalent to the hydrogel elongation properties in the hydrated state. If the core, or reinforcement member 8, was substantially lower in elongation properties, it could separate from the hydrogel causing the reinforcing member 8 to pull out of the hydrogel as force is applied. If, however, the swelling of the hydrogel was not in as confined a space and thus a substantially high normal force is not applied, a reinforcement member 8 with substantially lower elongation properties could be used.

In addition, it is important that there is sufficient interaction between the surface of the reinforcement member 8 and the hydrogel material. Since it is difficult for a bond to occur, such as the case with an adhesive, a physical interaction, such as a rough surface, is desirable. Thus, the reinforcement member 8 could be of a roughened monofilament creating minute "barbs" that would physically interact with the hydrogel, or preferably, the reinforcement member 8 could be of a non-roughened, multi-filament material that allows the hydrogel to be incorporated into its porous structure. In a preferred embodiment, the reinforcement member 8 is a polyester multi-filament braid or twist embedded along the axis of the hydrogel material.

In one embodiment, the plug contains one or more reinforcement members 8 running axially through and approximately centered in the interior hydrogel material, as shown in FIG. 1. Alternatively, the reinforcement member 8 can be located along the outer surface of the hydrogel. The reinforcement member 8 may comprise fibers. The fibers are advantageously at least partially orientated along the axis of the body 4 in order to allow the body 4 to swell radially, but at the same time preventing expansion in the axial direction. In one embodiment, the fibers are orientated in a braided manner along the outer surface of the hydrogel body 4. This aids in removal of the hydrogel body 4 by causing an inward force on the hydrogel when the fibers are placed under tension upon removal of the Device from the catheter. Such reinforcement members 8 can be made of the aforementioned polyester and polyurethane materials. Other reinforcing materials may be used, such as other polymer fibers, carbon fiber yarns, ceramic fibers, metal fibers, and others. The one or more reinforcement members 8, when employed along the outer surface, can act as an abrasive media to help remove biofilm from the catheter surface as the plug is removed from the catheter.

Figure 5:
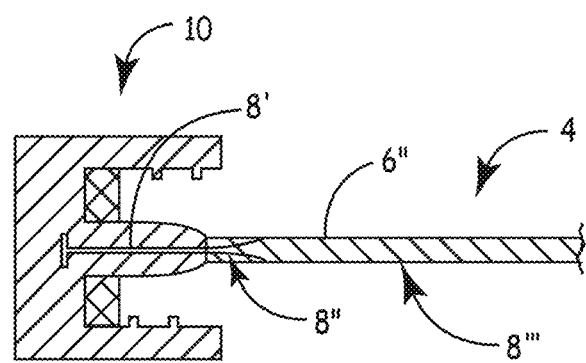
FIG. 5 is a side cross-sectional view of the proximal end of the hydrogel plug in its minimally hydrated state. The plug is shown with an alternate Luer connector and reinforcement member running from the connector axis to the outer surface of the plug.
Figure 5A:
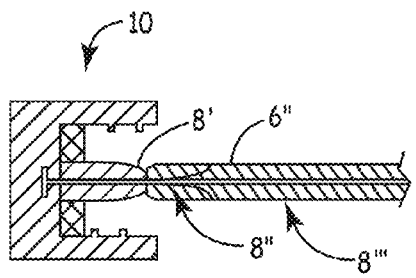
FIG. 5A is a side cross-sectional view of the proximal end of the hydrogel plug in its fully hydrated state. The hydrogel plug is shown with an alternate Luer connector and reinforcement member running from the connector axis to the outer surface of the plug.

Alternate embodiments for the location of the reinforcement member 8 and modified Luer connector 10 are shown in FIGS. 5 and 5A. The proximal reinforcement member 8' runs along the connector 10 axis similar to FIGS. 1 and 3. However, after leaving the connector 10, the reinforcement member 8" transitions from running along the axis to running along the circumference of the hydrogel body 4, shown as the distal reinforcement member 8'''. In this embodiment, the reinforcement member 8''' partially exits the hydrated hydrogel 6" to provide a more abrasive surface for better removal of biofilm within a catheter 100.

Figure 6:
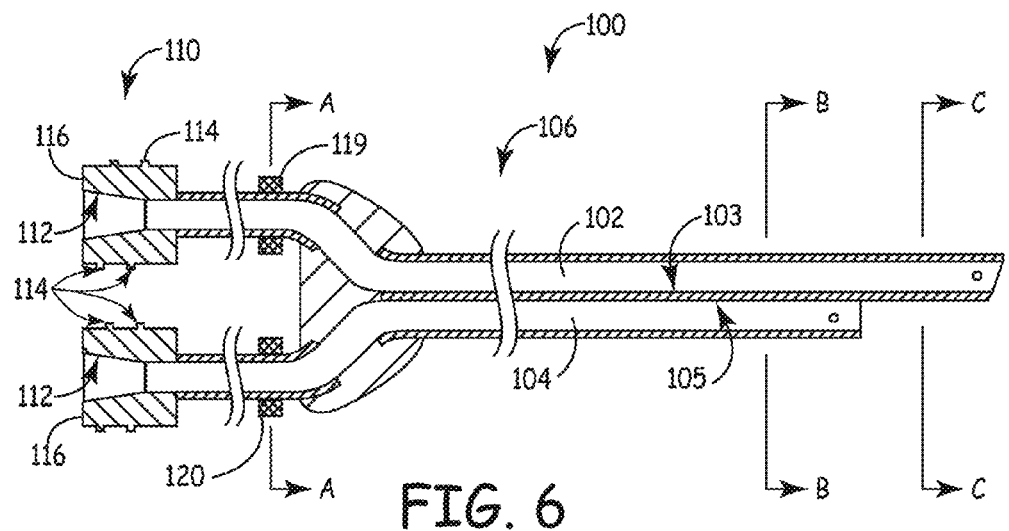
FIG. 6 is a side cross-sectional view of a hemodialysis catheter.

FIG. 6 shows a catheter 100. The catheter 100 illustrates one specific example embodiment of a medical device that can be used with the invention. This example is not meant to limit the use of the invention with other medical devices, but instead it is intended for illustrative purposes. The catheter 100 shown comprises the catheter body 106 and two catheter connectors 110. The catheter body 106 is generally a flexible tubular member that contains a venous lumen 102 having a venous lumen wall 103, and an arterial lumen 104 having an arterial lumen wall 105. The catheter connector 110 contains a catheter taper 112, a catheter thread 114 and a flat end 116, which is located on the most proximal portion of the catheter 100. Also shown in FIG. 6 are locations for a catheter clamp-venous 119 and catheter clamp-arterial 120. Such clamps are common in industry and are not shown in detail.

Figure 6A:
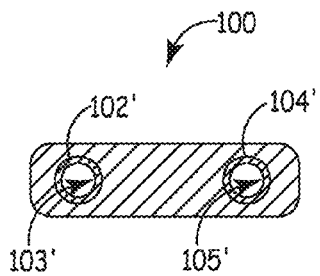
FIG. 6A is a cross-sectional view of the catheter taken along line A-A.
Figure 6B:
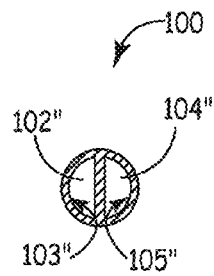
FIG. 6B is a cross-sectional view of the catheter taken along line B-B.
Figure 6C:
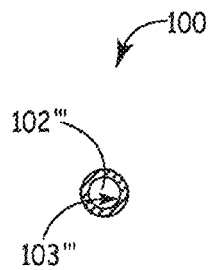
FIG. 6C is a cross-sectional view of the catheter taken along line C-C.

FIGS. 6A, 6B, and 6C illustrate how the arterial lumen 104 and the venous lumen 102 typically change shape along the length of the catheter 100. At the proximal end of the catheter 100, the proximal arterial lumen 104' and the proximal venous lumen 102' have round cross-sectional shapes as defined by the lumen walls 103' and 105'. In the middle region of the catheter 100, the mid arterial lumen 104" and the mid venous lumen 102" typically have D-shapes as defined by the lumen walls 103" and 105". In the distal end of the catheter 100, the distal venous lumen has a round shape as defined by the distal venous lumen wall 103''', and the arterial lumen 104 has terminated previous to distal region.

FIG. 7 shows two hydrogel plugs 2 inserted into a catheter 100: one in the catheter venous lumen 102 and the other in the catheter arterial lumen 104. In practice, the catheter lumens 102, 104 are filled with either saline, heparin lock, or an antimicrobial agent. Preferably, the antimicrobial agent is incorporated into the body of the hydrogel plug 4 and/or applied to the outer surface of the hydrogel plug 5. When the hydrogel plug 2 is inserted into the catheter 100, there is a gap between the lumen walls 103, 105 and the hydrogel outer surface 5, as shown in FIGS. 6A, 6B, and 6C. The gap allows the hydrogel to be advanced into the catheter 100 while at the same time minimizing the risk of pushing infectious biofilm from the lumen walls 103, 105 into the bloodstream. The length of the hydrogel plugs 2 may be selected to match the length of the catheter 100 such that the hydrogel plug tips 3 are close to the catheter tips 108, 109. In an example embodiment, the hydrogel plug tips 3 remain a few millimeters inside the catheter 100. In a preferred embodiment, the hydrogel body 4 extends approximately 20 centimeters into the catheter 100. In practice, this single length of hydrogel plug 2 will fit with all chronic hemodialysis catheters 100 that are commonly in use. In alternative embodiments, the hydrogel plug tips 3 may extend several millimeters outside of the catheter 100 or they may be shorter than the length of the catheter 100. When the hydrogel plug 2 is inserted into the catheter 100, the minimally hydrated hydrogel 6' begins to swell upon contact with fluid. In one embodiment, an elongate member 2 does not comprise hydrogel but is configured to expand upon contact with fluid in the catheter 100.

FIGS. 8, 8A, 8B, and 8C show one embodiment of fully hydrated hydrogel 6" after it has absorbed fluid and become fully swollen. In practice, fluid is absorbed, and the elongate member continues to swell until it reaches an equilibrium state. In the preferred embodiment, the hydrogel body 4 swells substantially anisotropically, swelling substantially in diameter but with minimal change in length. That state is determined by the properties of the hydrogel material and the fluidic environment to which the hydrogel is exposed. In one embodiment the hydrogel outer surface 5 contacts the catheter lumen walls 103, 105, and the hydrogel outer surface 5 conforms to the shape of the catheter lumen walls 103, 105. In one embodiment, the expandable portion of the elongate member 2 is configured to provide a barrier against fluid flow into and out of the catheter upon expansion of the expandable portion. This helps in the prevention and treatment of infectious microbes because the hydrogel outer surface 5 holds the antimicrobial agent against any infectious organisms that would be attached to the catheter lumen walls 103, 105, thus helping eliminate or prevent the growth infectious organisms. The contour fit also physically confines any infectious microbes, preventing further growth and transmission to other parts of the catheter 100 or the bloodstream where it could produce a systemic infection. However, depending on the antimicrobial agent used, their diffusion properties, and rate of kill, it may not be necessary for the fully or minimally hydrated hydrogel outer surface 5 to contact the catheter lumen walls 103 and 105.

Such an embodiment has distinct advantages and disadvantages. One advantage would make the hydrogel body 4 in its fully hydrated state 6" easier to remove since the contact force between the outer surface of the hydrogel 5 and the catheter lumen walls 103, 105 would be greatly reduced. A disadvantage would be that the antimicrobial agent eluting from the hydrogel body 4 would not be as confined and therefore possible to move through the catheter lumens 102, 104.

In one embodiment, the elongate member 2, upon expansion of the expandable portion, remains readily removable from the catheter as a single piece. Upon removal of the plug 2 from the catheter 100, the wall 5 rubs against the catheter lumen walls 103, 105, which produces a scrubbing action to further disrupt and remove adherent biofilm. In practice, hemodialysis patients have the hydrogel plugs 2 removed and replaced with new plugs 2 at every dialysis session, typically two or three times per week. The regular replacement of the plug 2 makes a significant improvement in controlling infection in dialysis patients.

Figure 8:
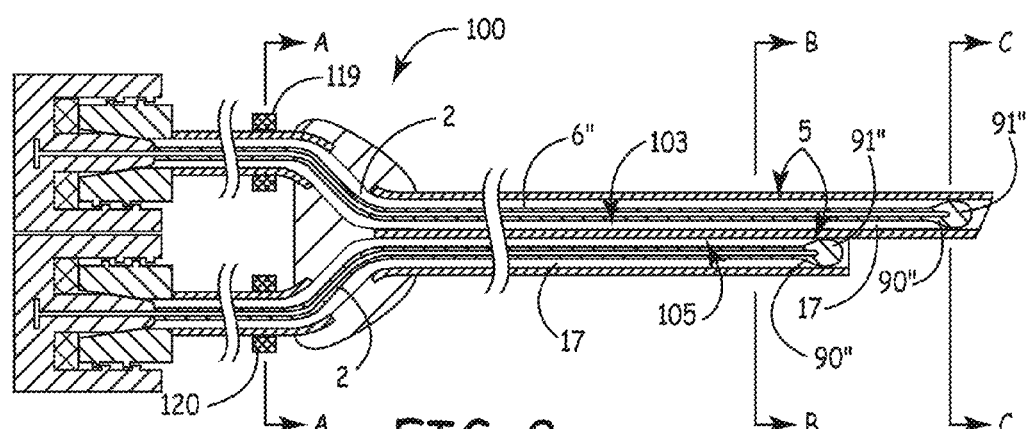
FIG. 8 is a side cross-sectional view of two fully hydrated hydrogel plugs in each of the catheter lumens.
Figure 8A:
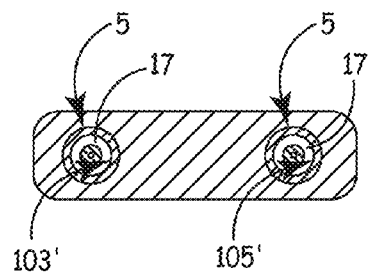
FIG. 8A is a cross-sectional view of the fully hydrated hydrogel plugs and catheter taken along line A-A.
Figure 8B:
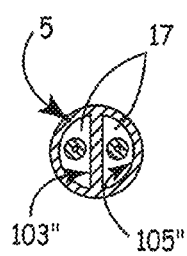
FIG. 8B is a cross-sectional view of the fully hydrated hydrogel plugs and catheter taken along line B-B.
Figure 8C:
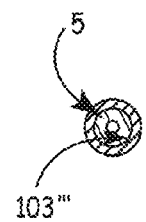
FIG. 8C is a cross-sectional view of the fully hydrated hydrogel plugs and catheter taken along line C-C.

In another embodiment, the elongate member, or plug 90", has a proximate portion and a distal portion 91", wherein the distal portion 91" of the elongate member has expanded, as in FIGS. 8, 8A, 8B, and 8C. As shown in FIG. 8, a contained volume 17 is formed by the expanded diameter of the distal portion 91" of the elongate member. The contained volume 17 is defined by the elongate member 90" and the lumen walls 103, 105. As shown in FIG. 8A, at the proximal portion of the elongate member 90" along the A-A line, the elongate member 90" has a diameter that is smaller than the diameter of the catheter lumen, defining the contained volume 17 around the elongate member 90" and within the lumen walls 103', 105'. The same is true along the B-B line shown in FIG. 8B, as the contained volume 17 is around the elongate member 90" and within the lumen walls 103", 105". At the distal portion 91" of the elongate member 90" along the C-C line shown in FIG. 8C, however, the expanded diameter is greater, providing a barrier to fluid flow within the lumen at that point and containing the volume 17. In one embodiment, a liquid, such as, for example, an antimicrobial agent, may fill or partially fill the volume 17.

Figure 9:
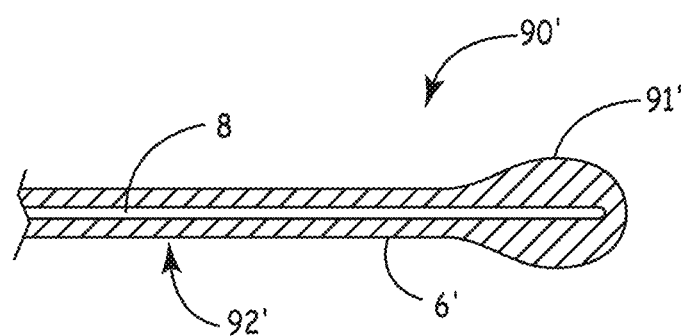
FIG. 9 is a cross-sectional view of the minimally hydrated hydrogel plug with a reduced diameter except in the tip region.
Figure 9A:
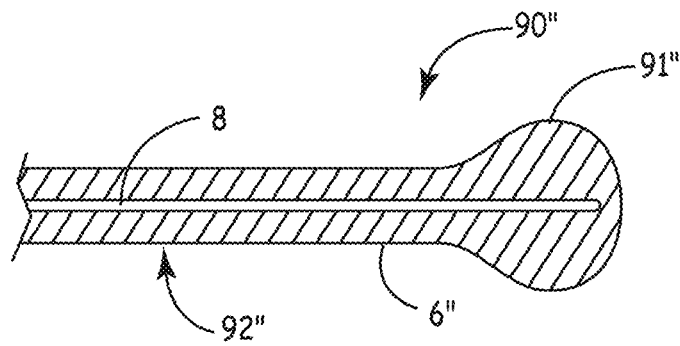
FIG. 9A is a cross-sectional view of the fully hydrated hydrogel plug with a reduced diameter except in the tip region.

FIG. 9 shows the minimally hydrated hydrogel plug 90' with the hydrogel body 6' possessing a smaller cross-sectional area than the distal tip 91' on the distal portion of the elongate member. A reinforcement member 8 is incorporated into the hydrogel plug 90' to strengthen the hydrogel plug. The distal tip 91' is preferably from 1 to 10 mm in length. When the hydrogel plug 90' is hydrated, as in FIG. 9A, the distal tip 91" on the distal portion of the elongate member swells such that it preferably fully contacts the catheter lumen wall, as previously described. In one embodiment, only a distal portion of the hydrogel is configured to expand so as to create a barrier to fluid flow through the lumen. In another embodiment, both the distal portion of the elongate member and the proximate portion of the elongate member are configured to expand, but the expanded diameter of the proximate portion is smaller than that of the distal portion of the elongate member.

In one embodiment, the hydrogel body 92' has a smaller cross-sectional area than the distal tip 91' on the distal portion of the elongate member, so its swollen cross-sectional area is also smaller than the tip 91". This smaller portion of the body 92" preferably stops swelling before it fully contacts the catheter lumen. In this preferred embodiment, where only the tip 91" of the plug 90" makes full contact with the catheter lumen wall 103, the force required to remove the plug 90" from the catheter 100 is substantially reduced. In another embodiment, a non-hydrogel-comprising elongate member, or plug 90', has a distal portion and a proximate portion, wherein the distal portion of the elongate member has an expanded diameter greater than that of the proximate portion.

Another embodiment of the Device comprises a hydrogel material in which the distal tip is, for example, 10 millimeters long, and is substantially larger in diameter and/or volume compared to its proximal region. This is such that when the hydrogel is hydrated, swelling of the larger distal tip is constrained by the catheter lumen, and the swelling fills up and displaces the volume of fluid in the catheter at that location. The proximal region is smaller in diameter and/or volume such that when it is hydrated and swells or expands, it is not constrained by the catheter lumen. This makes the Device easier to remove since the normal force applied to the catheter lumen is substantially reduced. In addition, the catheter lumen at the location of the larger hydrogel diameter and/or volume is substantially occluded resulting in minimal, if any, transfer of fluid past the larger distal tip from the catheter to the patient.

In one embodiment of the present invention, the hydrogel used is polyvinyl alcohol. Unlike the many other hydrogels, it is not cross-linked; its insolubility in aqueous media is due to its partially crystalline structures. Additional potential plug materials include, but are not limited to, silicone hydrogels, polyurethanes, polyureas, poly(caprolactams), gelatins, poly (acrylic acid), poly(acrylamides), poly(amides), poly(ethyleneimine), cross-linked polyethylene oxide, polyAMPS, polyvinylpyrrolidone, sodium polyacrylate, acrylate polymers and copolymers, lightly cross-linked biocompatible homopolymers and copolymers of hydrophilic monomers such as 2-hydroxyalkyl acrylates and methacrylates, e.g., 2-hydroxyethyl methacrylate (HEMA); N-vinyl monomers, for example, N-vinyl-2-pyrrolidone (N-VP); ethylenically unsaturated acids, for example, methacrylic acid (MA) and ethylenically unsaturated bases such as 2-(diethylamino) ethyl methacrylate (DEAEMA). The copolymers may further include residues from non-hydrophilic monomers such as alkyl methacrylates, for example, methyl methacrylate (MMA), partially hydrolyzed poly(acrylonitrile) and the like. The cross-linked polymers are formed by known methods in the presence of cross-linking agents, such as ethyleneglycol dimethacrylate and methylenebis (acrylamide), and initiators such as 2,2-azobis (isobutyronitrile, benzoyl peroxide, and the like. In addition, the above named compounds may be used as copolymers and blends derived therefrom. Methods for the preparation of these polymers and copolymers are well known to the art. The EWC (equilibrium water content) of these hydrogels can vary, e.g., from about 38% for Polymacon™ (poly HEMA) to about 79% for Lidofilcon™ B (a copolymer of N-VP and MMA) under ambient conditions. Methods for preparing partially hydrolyzed polyacrylonitrile hydrogels of different water contents and mechanical properties have been disclosed in the U.S. Pat. Nos. 4,337,327; 4,370,451; 4,331,783; 4,369,294; 4,420,589; 4,379,874; and 4,631,188. A preferred embodiment has 80% equilibrium water content in a poly(acrylonitrile-co-acrylamide). While a hydrogel is the preferred swellable material, such as a block copolymer of acrylonitrile and acrylamide (U.S. Pat. No. 6,232,406) which has an equilibrium water content of 38-90% by weight, this is not intended to limit the scope of the invention. Other materials that slowly increase in size or change shape when wetted may be used, such as fiber matrix or sponge of cross-linked carboxyalkylcelluloses fibers or other expandable, including flexibly expandable, material.

Antimicrobial Agent

An antimicrobial agent can be incorporated both into the elongate member material and/or on the elongate member surface of the present invention. In a preferred embodiment, an antimicrobial composition is located within the hydrogel of the elongate member 2 and elutes from the hydrogel after insertion of the elongate member 2 into a catheter. When the plug 2 is inserted into the catheter, the plug 2 begins to swell until it conforms to the lumen wall, bringing the antimicrobial agent into contact with infectious organisms that might be present along the lumen wall of the catheter or in solution. Additionally, the antimicrobial agent and any infectious organisms are confined together in the small space along the wall of the catheter. This confinement prevents dilution from body fluids, which would enter the catheter through the distal tip if the plug 2 was not present. Additionally, the plug 2 confines any antimicrobial agent leaching out of the plug to further increase the concentration of antimicrobial agent along the lumen wall where it is needed most. Another benefit is that the confining action of the plug traps any infectious microbes in a tight space along the lumen wall and prevents them from being transmitted to other areas of the catheter or to the body to prevent a systemic infection.

In an alternate embodiment, the antimicrobial agent is separate from the plug 2 so it can be injected into the catheter before, during, or after the plug 2 is inserted into the catheter.

The antimicrobial agents should kill and/or provide stasis of Gram-positive and Gram-negative bacteria and fungi. Preferably, the agents will also have efficacy at killing organisms within an established biofilm and/or degrading the extracellular matrix of the film. One suitable antimicrobial agent is tetrasodium ethylenediaminetetraacetic acid (tetrasodium EDTA). However, alternative antimicrobial agents may be used. Potential antimicrobial agents include, but are not limited to Trisodium citrate (with a typical concentration of 46.7% or higher), ciprofloxacin, liposomal ciprofloxacin, rifampin, minocycline, aminoglycosides, fluoroquinolones, vancomycin, netilmicin, fosfomycin, ceftriaxone, gentamicin, aztreonam, amphotericin B 1, fluconazole, taurolidine, disodium EDTA, 5-Fluorouracil, guanidinium thiocyanate, and sodium hydroxide (NaOH), teicoplanin, silver compounds, silver sulfadiazine, silver lactate, silver ions, copper sulfate, triclosan, chlorhexidine, chlorhexidine gluconate, aminoglycosides, fluoroquinolones, quaternary ammonium salts, peroxides, nanoparticles, including those of zinc oxide and titanium dioxide, sulfonamides, essential oils (sideritis, oregano oil, tea tree oil, mint oil, clove oil, nigella sativa, onion oil, phytoncides, leleshwa oil, lavender oil, lemon oil, lemon myrtle oil, neem oil, eucalyptus oil, peppermint oil, cinnamon oil, clove oil, thyme oil), cations and elements ($Cu^{2+}$, and colloidal silver), chemical biocide and disinfectants (hypochlorite to release chlorine, sodium dichloro-s-triazinetrione, alcohols (ethanol or isopropanol), aldehydes (glutaraldehyde, ortho-phthalaldehyde, formaldehyde), oxidizing agents (chlorine, sodium hypochlorite, calcium hypochlorite, hypochlorous acid, hypobromite solutions, chloramine, chloramine-T, chlorine dioxide, sodium chlorite, sodium chlorate, potassium chlorate, hydrogen peroxide, iodine, sodium chloride, peracetic acid, performic acid, potassium permanganate, potassium peroxymonosulfate), phenolics (phenol, carbolic acid, O-phenylphenol, chloroxylenol, hexachlorophene, thymol), quaternary ammonium compounds (benzalkonium chloride), trimethylolpropane, acetylsalicylic acid, dyes (methylene blue, Congo red, Disperse red, phthalocyanine blue, phthalocyanine green, gentian violet, etc.), surfactants (e.g., sodium dodecyl sulfate), parabens (methyl, ethyl and propyl), and biguanide polymer (polyaminopropyl biguanide is specifically bactericidal at very low concentrations (10 mg/l)).

While one particular drug or antimicrobial agent may provide relief from a wide range of challenging organisms that could potentially lead to catheter-related bloodstream infection, it is preferred to use a combination of two or more agents to further increase efficacy against a broad range of infectious organisms (bacteria and fungi).

In particular, catheter-related infections arise from three broad classes of organisms: fungi, Gram-negative bacteria, and Gram-positive bacteria. If an antimicrobial agent can be identified that would abate one or two of these types of organisms, while this would certainly be beneficial, it would leave the patient vulnerable to the remaining type(s). By pairing agents with different modes of action, infections by an increased spectrum of microorganisms can be prevented. This synergy would likely lead to further decreases in catheter-related morbidity and mortality, lessening the impact of the implanted catheter on the patient's quality of life. The preferred combinations of antimicrobial agents are chlorhexidine gluconate and EDTA, silver sulfadiazine and sodium dodecyl sulfate, and silver sulfadiazine and methylene blue.

Although treating, preventing, and eliminating infectious organisms for the prevention of infections is the primary use of the Device, ancillary benefits can also be envisioned which would involve incorporating additional agents. An antithrombotic agent eluting from the hydrogel can be used to improve the action of the heparin used currently in the locking solution. An enzyme or agent which promoted degradation of the extra-cellular matrix of biofilm (generally composed of polysaccharides) could enable use of the Device for treatment as well as prevention. If new treatments arise for antibiotic-resistant bacteria, these could also be introduced to contain the spread of these "superbugs."

Therefore, antimicrobials may be used in conjunction with antithrombotic agents, such as heparin or citrate and/or antimicrobial agents. Examples of combinations include, but are not limited to, cefazolin-heparin, ticarcillin-clavulanic acid-heparin, chlorhexidine-silver sulfadiazine, and ceftazidime-heparin.

In principle, antibiotics (rifampin, minocycline, etc.) can be incorporated into the Device or similar device and be as effective as non-antibiotic antimicrobials. However, continuous exposure to one antibiotic can lead to antibiotic resistant bacteria strains, for example, methicillin resistant *S. aureus* (MRSA). Therefore, the preferred embodiment uses an antimicrobial agent selected from the subset of those which are not antibiotics. If, for some reason, an antibiotic is used, the risk of developing antibiotic resistant strains of bacteria may be mitigated by preparing a second, complimentary, device containing a different antibiotic. By using the two devices in an alternating fashion with successive dialysis treatments, infectious organisms that are resistant to one antibiotic may be killed by the other.

Methods of Incorporating Antimicrobial Agents into a Hydrogel Matrix

While it is important to recognize the importance of both the antimicrobial agent used and the materials (e.g., hydrogels) into which they are incorporated, it is equally important to disclose how this is to be accomplished. Therefore, the following paragraphs disclose some preferred methods of incorporating such antimicrobial agents into a hydrogel matrix.

One method of loading the antimicrobial into the hydrogel is to physically blend it with the polymer during processing and/or shaping. This produces good uniformity of mixing and allows quantitative determination of the amount of antimicrobial agent loaded. Care should be taken, however, to assure that neither the physical properties of the hydrogel nor the activity of the antimicrobial is adversely affected.

The swelling properties during synthesis of the hydrogel can also be exploited to assist incorporation of the antimicrobial agents. As the gel swells, its pore size increases. Thus, allowing the gel to swell in a solution of the antimicrobial will cause the antimicrobial to diffuse into the bulk of the gel. The driving force for this diffusion is the concentration difference, which also drives the antimicrobial to elute from the Device into the catheter lumen during use.

In some hydrogel/solvent interactions, especially those involving water as the solvent, the degree of swelling can become undesirably large (ca. 50 to 100× original weight). This can cause the gel to become very weak and hard to process. This can be mitigated by adding a small-molecule solute (such as sodium chloride) to the solution. The solute causes an osmotic pressure, which opposes the swelling of the gel with the tendency of the solvent to dilute the solute.

There are further considerations which affect loading of the agent into the hydrogel. The partition coefficient, k, is a ratio of the compatibility of the antimicrobial and the hydrogel matrix relative to the compatibility of the antimicrobial and water (or other swelling solvent). Thus, it is not possible to predict the final percent weight of the agent that has infiltrated into the dried gel.

Similarly, manipulation of pH (and its control by buffering) can be used to tailor the antimicrobial to the hydrogel. The degree of protonation of Lewis acids (e.g., EDTA) is affected by solution pH. Generally, more protonation will increase compatibility with the hydrogel, and this can be achieved by holding pH near neutral (6.0-8.0).

Physical methods may also be used to improve the antimicrobial loading process either in terms of reducing processing time or increasing the amount loaded. Application of heat and pressure may increase the rate and extent of loading. Also, the partition coefficient, k, is generally a function of temperature and pressure, so thermodynamic equilibrium may be manipulated to favor a greater concentration of antimicrobial agent within the hydrogel. Sonication is another process known in the art as a means for reducing hydration time of the hydrogel. However, once full hydration is achieved, or nearly so, sonication should be stopped since it has the potential to damage the physical integrity of the hydrogel.

Once the hydrogel is swollen with a solution of the desired antimicrobial agent, it can be dried under ambient conditions, or, if desired, in a vacuum. This will remove the solvent from the original solution, leaving the antimicrobial entrained within the pore structure of the hydrogel. Conceivably, the hydrogel could also be coated using a solution in a solvent that does not swell the hydrogel. However, this would leave the antimicrobial on the hydrogel as a surface layer only.

Another component of the present invention is its ability to be easily inserted and removed from any catheter of suitable size (internal diameter and length). Since the Device is inserted relatively dry and of a smaller size (outside diameter) than the internal diameter of the catheter, it can be inserted with little difficulty. However, after the Device has had time to absorb the liquid present or added, it will swell and preferably conform to the interior geometry of the catheter. Thus, it is important that the Device be configured to be easily removed. This can be accomplished by the addition of a lubricious coating applied to the material comprising the Device.

In the preferred embodiment, hydrogel material is used, which is subsequently hydrated; hydrated hydrogels inherently have low coefficients of friction. Friction typically decreases with increasing water content, though at the expense of mechanical strength. This situation is true especially when the hydrogel swells sufficiently to contact the walls of the lumen. Thus, in these situations it may be desirable to provide a lubricious coating to ensure that the Device releases from the wall and slides out of the catheter. These, as well as processes for their application, are well-known in the art (i.e. U.S. Pat. Nos. 7,097,850; 7,442,402; and 6,444,318). An effective lubricious coating can be applied with a small enough (ca. 10 micron) film thickness that it will not be a substantial barrier to elution of the antimicrobial during use of the Device. Examples of substances that may be used as a lubricious coating include, but are not limited to, polyvinylpyrrolidone, polyvinyl alcohol, fluoropolymers, silicone fluids, silane, and other lubricious coatings known in the art for medical devices including light and/or heat activated systems.

Alternately, the lubricious coating itself may be used as the vehicle for delivering the antimicrobial agent. Such coatings are generally hydrophilic, with sufficient porosity to allow the infiltration of antimicrobials. In an alternative embodiment, a non-hydrogel substrate with such a coating is used.

In theory, because the total hydrogel coating volume is less than the non-hydrogel rod, the coating will not take up as much of the antimicrobial agent as a solid hydrogel rod. Therefore, the application of a coating to the inner diameter of the catheter lumen is an approach that has generated significant recent interest within the field. The drawback to this approach has been that the coating does not persist for the desired service time of the chronic catheter. In the present invention, as has been described, the coating is applied on the Device of the present invention rather than on the catheter lumen/wall and is renewed with each replacement of the device—generally three times a week—after each dialysis session.

Delivery System

Because the present invention is used to combat infections in patients who have their blood and/or other fluids accessed by a catheter, it is extremely important and desirable that the elongate member 2 does not inadvertently expose the dialysis patient to any additional bacterial contamination. Therefore, the plug 2 is provided sterile along with a delivery system 47 specifically designed for this purpose. For ease in explanation, the embodiments of the device described above, comprising an elongate member and antimicrobial composition, is collectively referred to in this section as "the Device."

Figure 10:
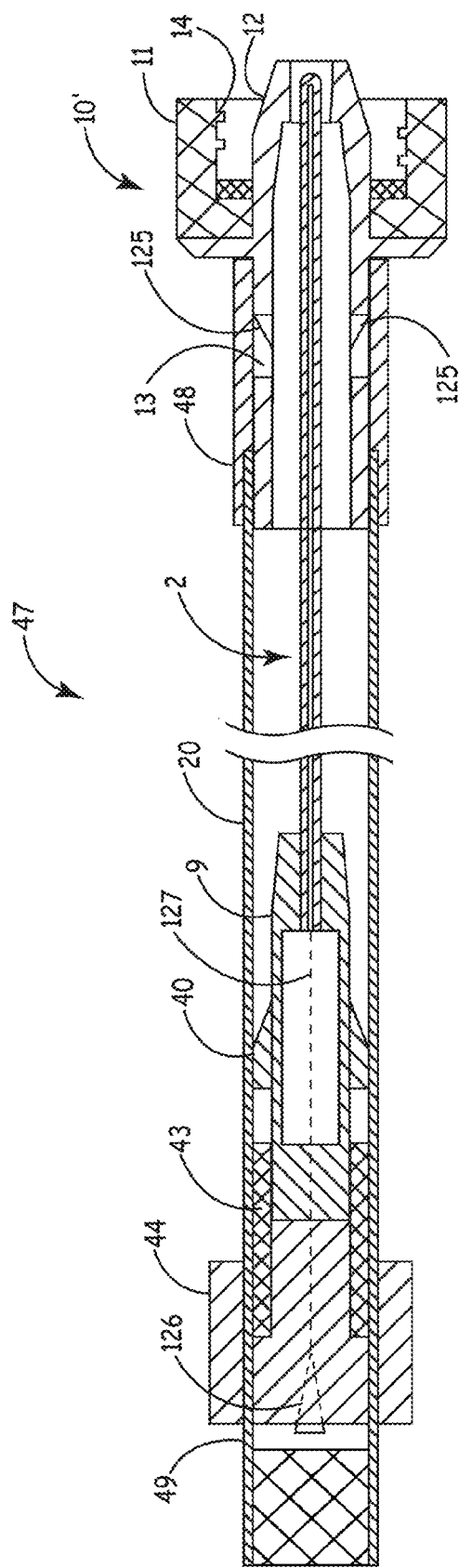
FIG. 10 is a cross-sectional view showing the minimally hydrated hydrogel plug in the delivery system prior to insertion into a catheter.

The delivery system 47, as shown in FIG. 10, ensures the Device is installed in the catheter properly and reduces the chance for inadvertent contamination from the surrounding environment. The delivery system 47 is used to easily deliver and deploy the plug into the lumen of a catheter, which substantially limits any additional contamination without the need for additional or special tools.

In a preferred embodiment, the invention is an apparatus for delivery of an elongate member into the lumen of a transdermal catheter, the apparatus comprising: a protective sheath 20 configured to at least substantially surround an elongate member 2; and slidable member 44 configured to travel along the protective sheath 20, the slidable member 44 operatively coupled to the elongate member 2; wherein the elongate member 2 is insertable into a lumen of a catheter by moving the slidable member 44 along at least a part of the length of the protective sheath 20.

In another embodiment, the invention comprises a protective sheath 20 configured to at least substantially surround an elongate member 2; a slidable member 44 configured to travel along the protective sheath 20, the slidable member 44 operatively coupled to the elongate member 2; and a connecting member positioned on the distal end of the protective sheath 20, the connecting member configured to lock onto the distal end of a catheter; wherein the elongate member 2 is insertable into a lumen of a catheter by moving the slidable member 44 along at least a part of the length of the protective sheath 20.

In one embodiment, the connecting member may be a modified male Luer® connector 10' that attaches to the female Luer connector, which is standard on most catheters, especially hemodialysis catheters. Also incorporated into the modified male Luer connector is one or more fixation mechanisms which lock the Device in place after the Device is inserted into the catheter, without the need for additional manipulation, handling, or tools that could contaminate the Device. In addition, a protective sheath 20 can be provided which further aids in preventing contamination during the insertion process. Furthermore, an aid can be provided that prevents the end user from touching and contaminating the Device.

FIG. 10 shows one embodiment of the delivery system 47. The hydrogel plug 2 is loaded into the delivery system 47 for easy and sterile insertion into the catheter 100 (not shown). The delivery system 47 comprises a modified male Luer connector 10' with cutouts 13, a shield coupler 48 with shield coupler locking arms 125 engaged in the modified male Luer connector cutouts 13, a hydrogel plug 2, a protective sheath 20, the connector insert 9 with connector insert protrusions 40, the connector insert/slidable member coupler 43, the slidable member 44, and the shield grip 49. The entire delivery system assembly 47 is packaged in a sterile package (not shown) prior to use. Two devices are used after each hemodialysis session. One is inserted into the catheter venous lumen 102, and the other is inserted into the catheter arterial lumen 104. By way of explanation, only the insertion of the hydrogel plug 2 into the catheter venous lumen 102 will be described. Insertion of the hydrogel plug 2 into the catheter arterial lumen 104 is identical.

After the hemodialysis machine (not shown) has been disconnected from the catheter venous connector 110, the catheter venous lumen 102 is purged of blood using a heparin/saline solution (not shown) and the catheter venous clamp 119 is closed. The delivery system assembly 47 is removed from its sterile packaging (not shown), and the delivery system assembly 47 is attached to the catheter connector 110 by inserting the modified male Luer connector taper 12 into one of the corresponding catheter Luer taper 112 and locking it in place with the locking ring 11 by engaging the modified male Luer connector locking threads 14 with the catheter female Luer connector with external locking threads 114.

The catheter venous clamp 119 is then opened and the shield grip 49 at the proximal end of the delivery system assembly 47 is grasped by one hand using the thumb and forefinger. Then, using the thumb and forefinger of the other hand, the slidable member 44 is grasped and in one fluid motion, the slidable member 40 is advanced towards the distal end of the delivery system 47. This action disengages the slidable member 44 from the protective sheath slidable member lock 126 moving the slidable member through the protective sheath slit 127 and advances the hydrogel plug 2 down the catheter venous lumen 102 of the catheter 100. In one embodiment, once the plug 2 has been deployed into the catheter venous lumen 102 of the catheter 100, the delivery system assembly 47 detaches from the connector 10'. The detachment of the delivery system 47 from the connector 10' may occur automatically. In one embodiment, this occurs when the connector insert protrusions 40 on the connector insert 9 engage the shield coupler locking arms 125 of the shield coupler 48 and force the shield coupler locking arms 125 out of the modified male Luer connector cutouts 13, causing a majority of the delivery system 47 to detach from the connector 10'. Remaining attached to the catheter 100 is the modified male Luer connector 10' with the connector insert 9 and the connector insert protrusions 40 engaged in the modified male Luer connector cutouts 13 and the locking ring 11 attached to the catheter modified male Luer connector with external threads. Deployed in the catheter venous lumen 102 is the plug 2. In yet another embodiment, the invention comprises a protective sheath 20 configured to at least substantially surround an elongate member 2; and a slidable member 44 configured to travel along the protective sheath 20, the slidable member 44 operatively coupled to the elongate member 2; wherein the elongate member 2, is insertable into a lumen of a trans-dermal catheter by moving the slidable member 44 along at least a part of the length of the protective sheath 20; and wherein the protective sheath 20 is further configured to detach from the elongate member 2 upon delivery of the elongate member 2 into the lumen of the trans-dermal catheter. In certain embodiments may further comprise a connecting member positioned on the distal end of the protective sheath 20, where the connecting member is configured to lock onto the distal end of the catheter. The connecting member may be further configured to detach from the protective sheath 20 and remain locked on the catheter upon delivery of the elongate member 2 into the lumen of the catheter. The connecting member may be a male Luer connector or modified Luer connector 10', as described above.

Furthermore, it is important to reduce exposure of healthcare providers to a patient's bodily fluids upon removal of the plug 2 or the entire Device. Bodily fluids from the dialysis patients would present a health risk to the healthcare provider if the fluids were allowed to come into contact with the provider. A protective cover, known as a removal sheath, is therefore provided in some embodiments to contain the plug 2 or the entire Device and any bodily fluid that may be lost while the plug 2 or the entire Device is being removed.

Figure 11:
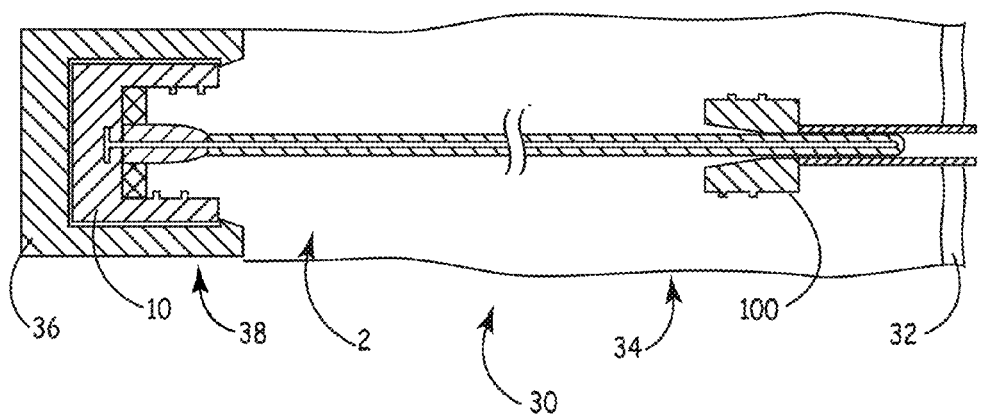
FIG. 11 is a cross-sectional view showing the fully hydrated hydrogel plug in the removal sheath prior to the plug is being removed from the catheter.
Figure 12:
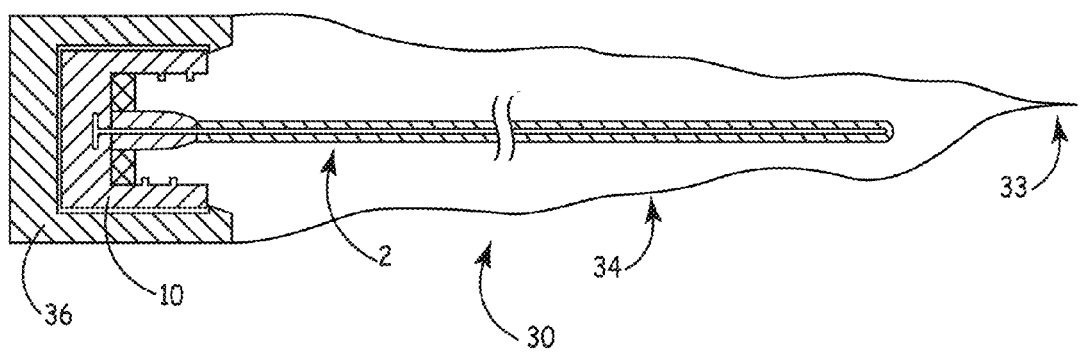
FIG. 12 is a cross-sectional view showing the fully hydrated hydrogel plug after it is withdrawn from a catheter and sealed in the removal sheath.

FIG. 11 shows the removal sheath 30 as the hydrogel plug 2 is being removed from the catheter 100. The process of removing the hydrogel plug 2 from the catheter 100 begins with the sheath cap 36 being firmly attached to the male Luer connector 10 such that the plug cap 10 may be unscrewed by rotation of the sheath cap 36. Next, the adhesive strip 32, with its protective paper still attached (not shown), is slid over the male Luer connector 10. The hydrogel plug 2 is pulled out of the catheter 100 by grasping and pulling on the sheath cap 36. As the hydrogel plug 2 is pulled out, the sheath wall 34 is kept over the exposed length of the hydrogel plug 2 to ensure that the hydrogel plug 2 or any fluids do not contaminate the healthcare worker. After the hydrogel plug 2 is fully removed, the adhesive strip is sealed 33, as shown in FIG. 12.

Figure 13:
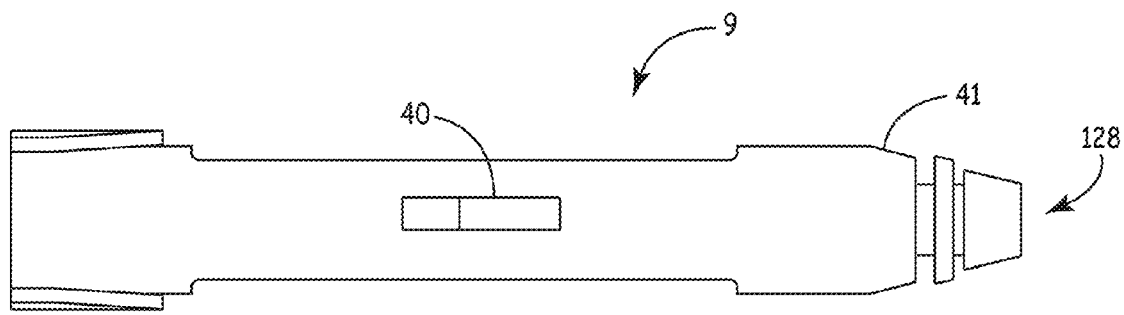
FIG. 13 is a top view of the delivery system connector insert.
Figure 13A:
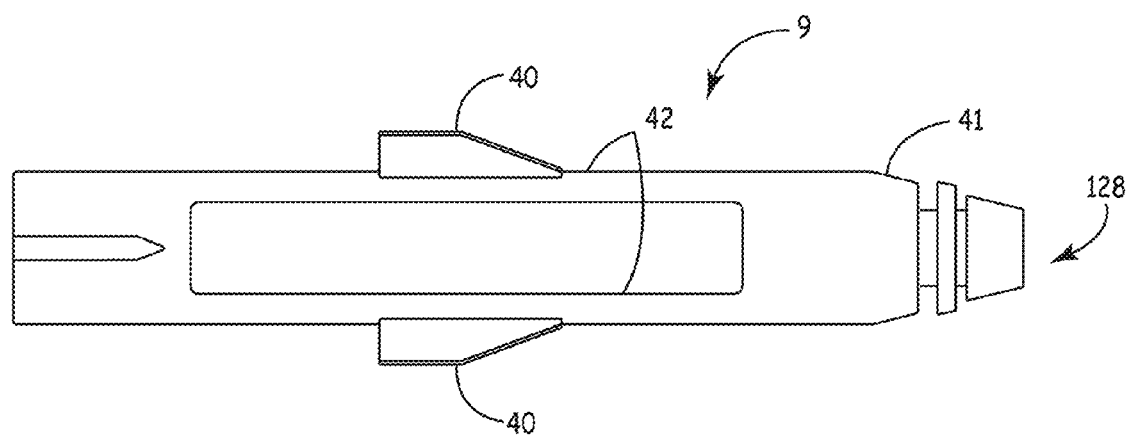
FIG. 13A is a side view of the delivery system connector insert.

FIGS. 13 and 13A shows the connector insert 9 in a top and side views, respectively, with connector insert protrusions 40, flexible member 42, and male taper 41. As the connector insert 9 is advanced and inserted into the modified male Luer connector insert hole 128, the connector protrusions 40 deflect inwards via its flexible member 42. Once positioned far enough into the modified male Luer connector insert hole 128, the connector insert protrusions 40 are allowed to return to their original, non-deflected state and expand outward into the modified male Luer connector cutouts. This locks the connector insert 9 into place, not allowing it to be easily removed.

Figure 14:
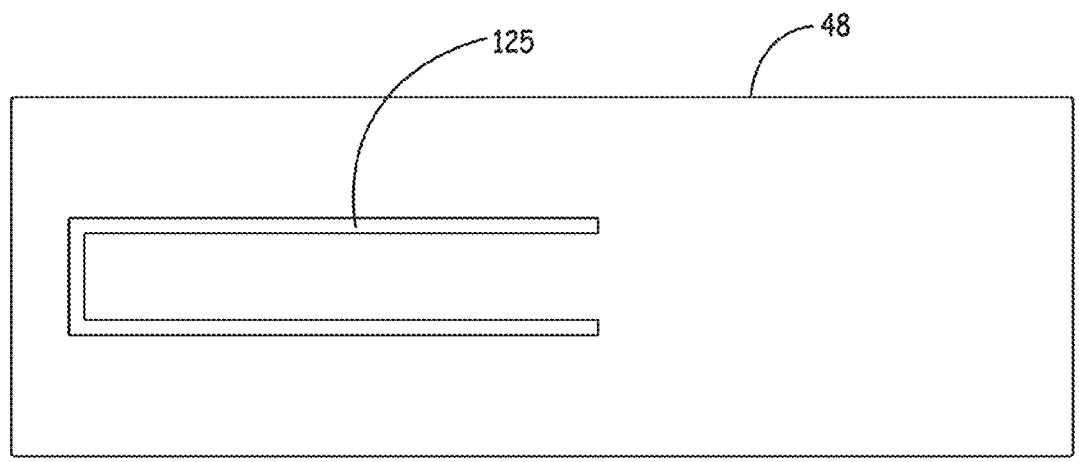
FIG. 14 is a top view of the delivery system shield coupler.
Figure 14A:
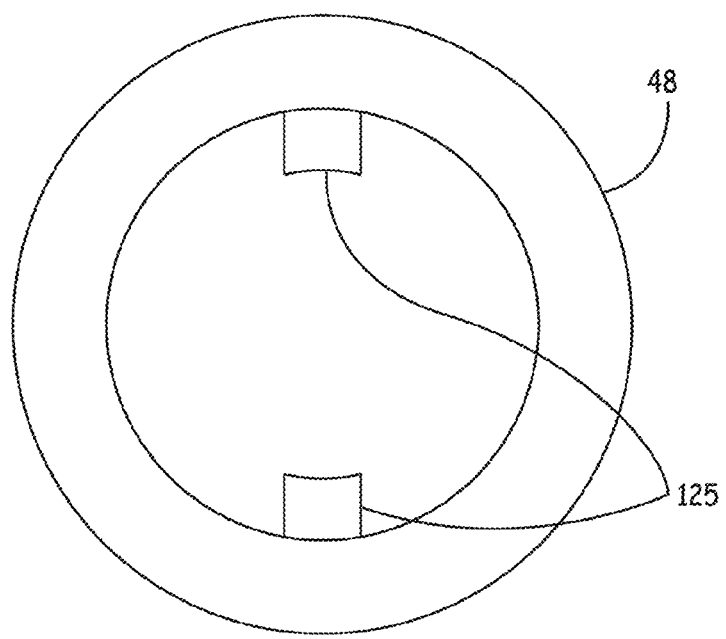
FIG. 14A is a end view of the delivery system shield coupler.
Figure 14B:
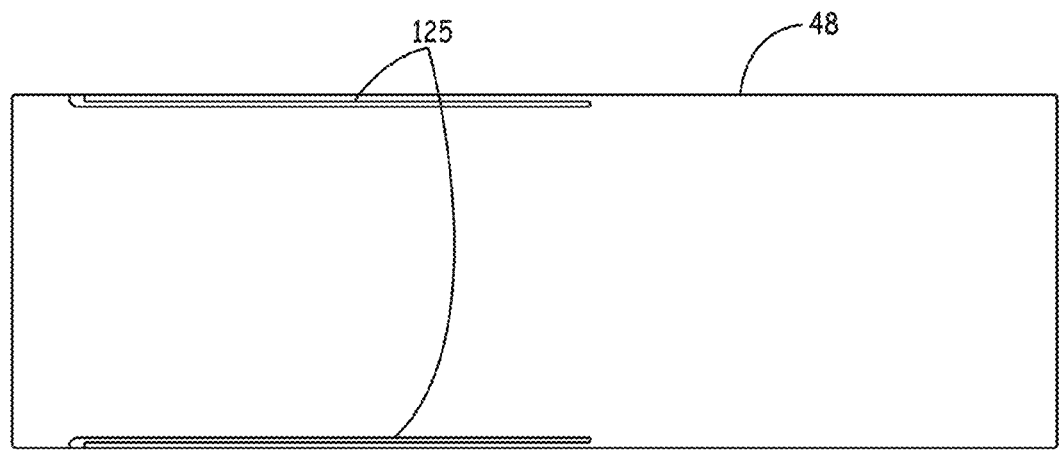
FIG. 14B is a side view of the delivery system shield couple.

In some embodiments, a shield coupler 48 is affixed to the protective sheath 20, which in turn may be mechanically attached, but not permanently attached, to the modified male Luer connector 10'. In another embodiment, the shield coupler 48 is permanently affixed to the protective sheath 20. The shield coupler 48 is roughly tubular in shape and comprises one or more flexible members which are cantilevered from the wall of the shield coupler 48 and fit into the rectangular cutouts in the wall of the modified male Luer connector 10'. FIGS. 14, 14A and 14B show the shield coupler 48 in top, end, and side views, respectively. The shield coupler 48 is fixed to the distal end of the protective sheath 20, and the shield coupler locking arms 125 are engaged in the modified male Luer connector cutouts 13 prior to deployment of the hydrogel plug 2 into the catheter lumen, 102, 104.

Figure 15:
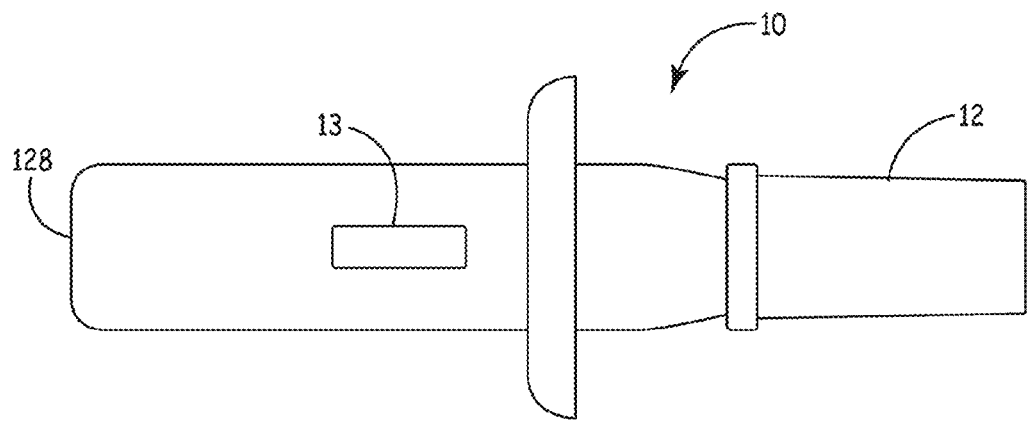
FIG. 15 is a top view of the delivery system modified male Luer connector.

FIG. 15 shows the modified male Luer connector 10 with connector cutouts 13, connector insert hole 128, and male Luer taper 12. The modified male Luer connector 10' is attached to the shield coupler 48 via the shield coupler locking arms 125. The shield couple 48 is bonded to the distal end of the protective sheath 20.

Figure 16:
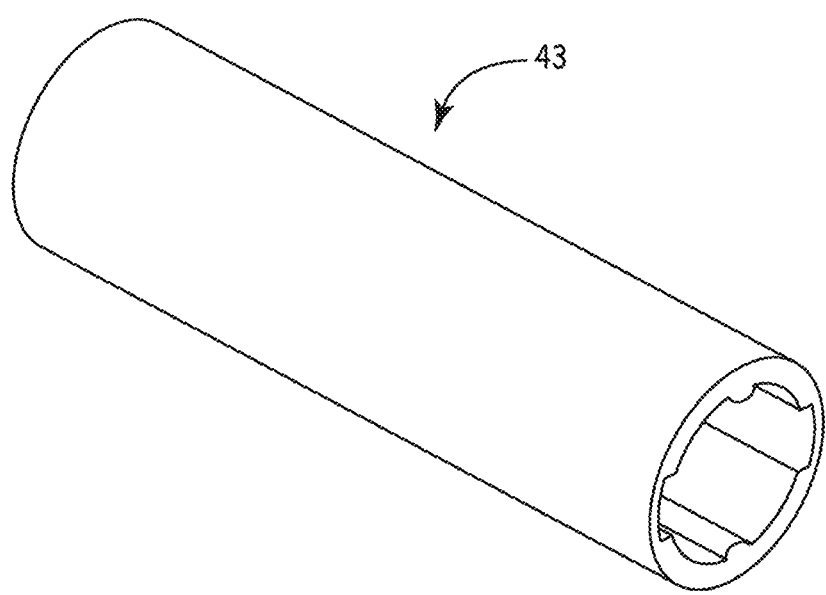
FIG. 16 is a prospective view of the delivery system connector insert-slidable member coupler.
Figure 17:
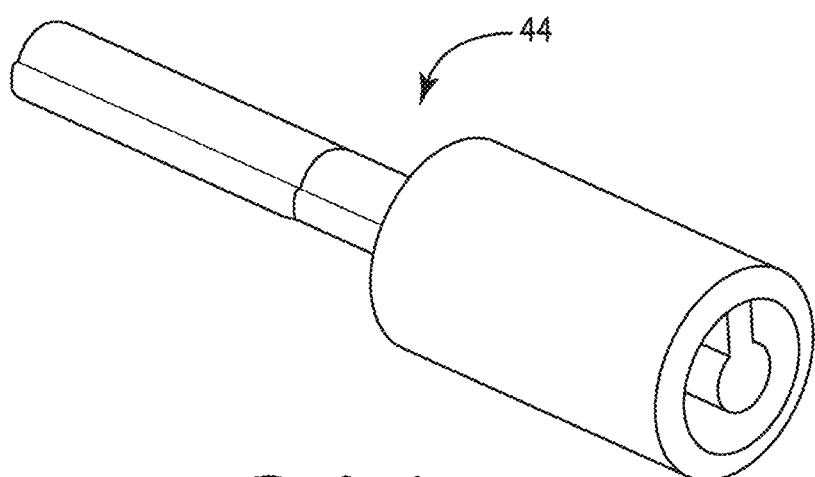
FIG. 17 is a prospective view of the delivery system slidable member.
Figure 17A:
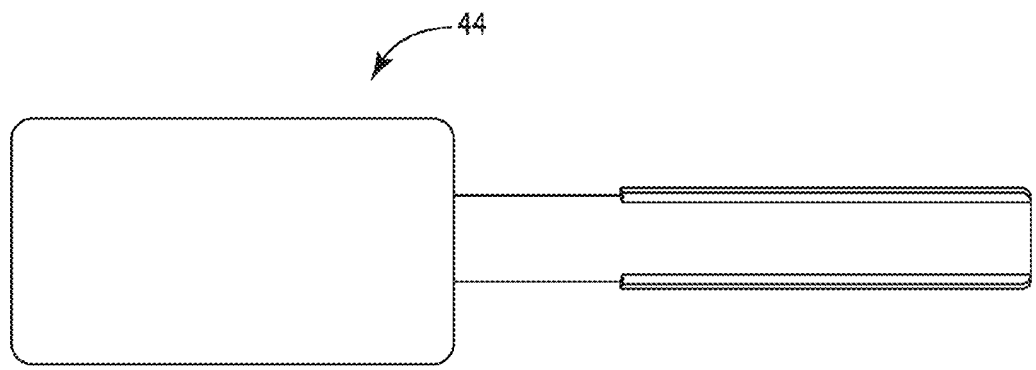
FIG. 17A is a side view of the delivery system slidable member.
Figure 17B:
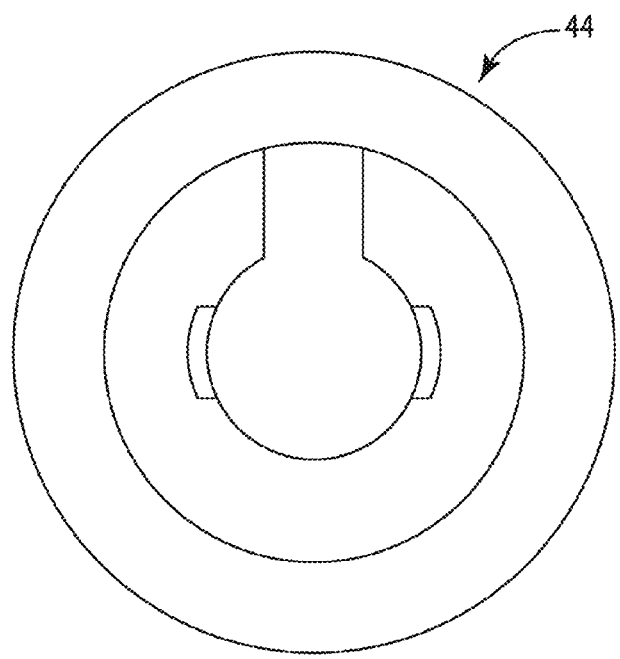
FIG. 17B is a left end view of the delivery system slidable member.
Figure 17C:
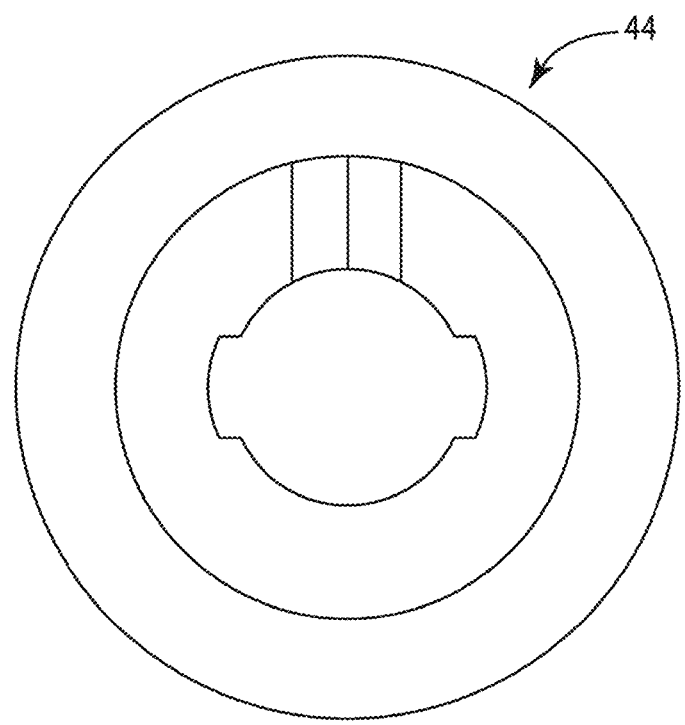
FIG. 17C is a right end view of the delivery system slidable member.

FIG. 16 shows the connector insert-slidable member coupler 43. The connector insert-slidable member coupler 43 connects the slidable member 44 and the connector insert 9 as part of the delivery system assembly 47. In addition to coupling the connector insert 9 with the slidable member 44, the connector insert-slidable member coupler 43 also allows the slidable member 44 to decouple from the connector insert 9 as it is pushed into the Luer connector.

The gripping mechanism or slidable member 44 attaches to the connector insert 9 for means of advancing the plug 2 through the delivery tool without touching the elongate member, plug 2. In one embodiment, the slidable member 44 has an inner portion and an outer portion, such that the inner portion is positioned within the sheath 20 and is in contact with the elongate member 2, and the outer portion is positioned outside of the sheath 20 and is configured for grasping by a user. In a preferred embodiment, the slidable member 44 is a hollow cylindrical shape with a protrusion affixed to the inside wall of the hollow cylinder and extending beyond the end of the hollow cylinder. This protrusion has one or more protrusions for orientation and connects to the connector insert/slidable member coupler 43, which in turn connects to the connector insert 9, allowing the slidable member 44 to decouple from the connector insert 9 as it is pushed into the connector and locking it in place. FIGS. 17, 17A, 17B and 17C show one embodiment of the slidable member 44 in perspective, side, left end, and right end views. The slidable member 44 is operatively coupled to the connector insert-slidable member coupler 43 and is further operatively coupled around the protective sheath 20 in order to slidably advance the connector insert 9 into the connecting member. In one embodiment, the slidable member 44 connects to the connector insert-slidable member coupler 43 and wraps around the protective sheath 20 in order to slidably advance the connector insert 9 into the modified male Luer connector 10. The slidable member 44 advances the connector insert-slidable member coupler 43 and connector insert 9 through the lumen of the protective sheath 20. As the slidable member 44 advances, the protective sheath slit 127 opens and closes around the slidable member 44 in order to limit inadvertent contamination of the hydrogel plug 2. In another embodiment, the slidable member 44 comprises an intermediate portion between the inner and outer portions, the intermediate portion configured to cut a path along the protective sheath 20. In yet another embodiment, the slidable member 44 is configured to lock onto the end of a catheter. In one embodiment, the protective sheath 20 is removable from the catheter upon locking the slidable member 44 to the catheter.

Figure 18:
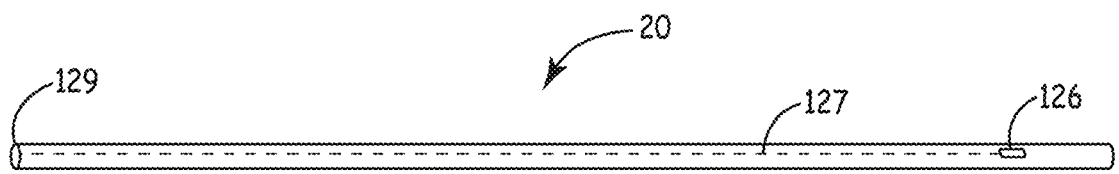
FIG. 18 is a perspective view of the delivery system shield tube.

The plug 2 is protected with a protective sheath 20 from contamination through handling. In one embodiment, the protective sheath 20 has a slot along at least a portion of its length. In another embodiment, the slot comprises an opening, or slit 127, along a portion of the length of the protective sheath 20. In a preferred embodiment, the protective sheath 20 is permanently attached to the shield coupler 48. The shield coupler 48 may be temporarily affixed to the modified male Luer connector 10'. The protective sheath 20 is made of a semi-rigid material with a slit 127 running substantially the length of the protective sheath 20. The slit alternately opens and closes in front and behind the slidable member as the slidable member is advanced from the proximal end to the distal end of the delivery tool. The protective sheath 20 can be made of a rigid or flexible material. In a preferred embodiment, the slit 127 is configured to open and close as the slidable member 44 is advanced through it. Examples of materials that may be used for the protective sheath 20 include, but are not limited to, polyvinylchloride (pvc), acrylonitrile-butadiene-styrene (abs), polystyrene, poly(tetrafluoroethylene) (PTFE), polypropylene, polyethylene (low/high density), acetal, nylon, polyethylene terephthalate (PET), polyethylene terephthalate glycol (PETG), polyurethane and polycarbonate. The very proximal portion of the protective sheath 20 is solid which provides a location for an individual to grip and balance the delivery tool as the hydrogel plug 2 is advanced. FIG. 18 shows the protective sheath 20 with protective sheath slidable member lock 126, protective sheath slit 127 and protective sheath distal end 129. The purpose of the protective sheath 20 is to limit inadvertent contamination of the hydrogel plug 2 while the hydrogel plug 2 is being advanced into the catheter lumen 102 or 104. In the embodiments in which slit 127 is partially or fully created as the slidable member 44 is advanced along the protective sheath 20, the protective nature of the sheath 20 is enhanced.

Figure 19:
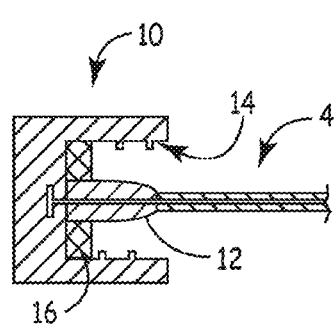
FIG. 19 is a cross-sectional view showing the modified male Luer connector and connector insert at the proximal end of the hydrogel plug. The modified male Luer connector is not connected to the catheter.
Figure 19A:
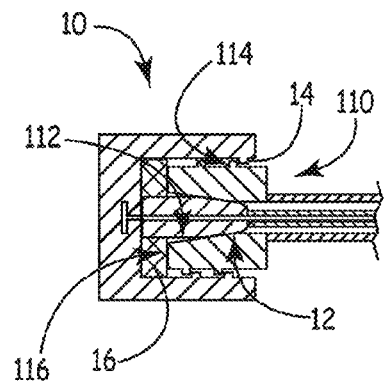
FIG. 19A is a cross-sectional view showing the modified male Luer connector at the proximal end of the hydrogel plug and catheter. The connector is connected to the catheter and the seal is deformed.

FIG. 19 shows the male Luer connector 10 along with a portion of the hydrogel body 4. Features of the male Luer connector 10 include the plug taper 12, the plug threads 14, and the contamination barrier 16. As the hydrogel plug is fully inserted into the catheter 100, the male Luer connector 10 engages the catheter connector 110 as shown in FIG. 19A. The male Luer connector 10 is rotated clockwise about its axis to engage the plug threads 14 with the catheter threads 114. This advances the male Luer connector 10 further into the catheter connector, causing the plug taper 12 to fully contact the catheter taper 112. These tapers 12, 112 can be standard Luer tapers.

The advancing male Luer connector 10 also causes the contamination barrier 16 to contact the flat surface 116. The contamination barrier 16 helps prevent infectious material from entering the catheter connector 110. The contamination barrier comprises polyurethane foam that is impregnated with an antimicrobial agent. The location of the barrier, the material of its construction, and the addition of an antimicrobial agent, as described above, may be varied. For example, the barrier 16 may be located at catheter 114 and contact the locking threads 14. Examples of materials that may be used for the barrier 16 include, but are not limited to, silicone rubber, polyisoprene, butyl rubber, polyurethane, polyester, polyvinyl alcohol, PVC; some of these materials may be formed as a foam, preferable closed cell, to aid in sealing.

Preferably, after manufacturing and prior to use, the delivery system is packed and a sealed in foil to maintain the desired level of hydration.

Alternative Embodiments

In one embodiment, the invention is a system for delivering an antimicrobial agent into the lumen of a trans-dermal catheter, the system comprising: an elongate member 2 configured for insertion into a lumen of a trans-dermal catheter, said elongate member having a distal portion configured to provide a barrier to fluid flow; and an antimicrobial composition positioned to be delivered into the catheter. The distal portion of the elongate member 2 may comprise a non-expanding barrier. Alternatively, the distal portion may comprise an expanding barrier. In another embodiment, the distal portion comprises a hydrogel, as described above in other embodiments.

In one embodiment of the present invention, it may be desirable to decrease the overall contact force by reducing the area of contact and/or the coefficient of friction between the catheter and the plug to make it easier to remove the plug from the catheter. This can be accomplished by reducing the diameter of the plug 2 over a substantial length such that when it is hydrated, the swollen plug applies very little, if any, normal force to the lumen of the catheter. Preferably, a short section of the plug is a larger diameter such that when it swells it does not contact the interior lumen of the catheter. Thus, the force to remove the plug 2 will be greatly reduced since the contact area is greatly reduced. Doing so helps to retain the ability of the plug 2 to act as a barrier and keep the antimicrobial agent from entering the bloodstream. The preferred embodiment consists of a short length at the distal tip, preferably less than 10 mm in length, more preferably less than 5 mm, and most preferably less than 2 mm, which is a sufficient swollen or expanded diameter to contact the catheter wall. The distal tip may further be configured to reduce the force it applies to the catheter lumen by applying fins or other geometry that flex and/or deform when the tip contacts the catheter lumen. This flexing action makes the distal tip less able to transmit force to the catheter wall.

In certain embodiments of the present invention, the elongate member 2 makes contact with the catheter wall, causing it to be in direct contact with the infectious organisms. When an infectious organism is present, the infectious organism creates a biofilm that adheres to the catheter wall. This biofilm acts as a barrier, protecting the infectious organism from antimicrobial agents. As the Device is removed from the catheter, the outer surface of the Device rubs on the inner walls of the catheter, causing a scrubbing action to separate the biofilm from the catheter wall.

In another embodiment of the invention, the distal portion of the elongate member 2 comprises a deformable member. The deformable member may be series of circular fins, bristles and/or ribs around a central core. The core should be flexible yet sufficiently rigid enough to be deployed down the lumen of a catheter. The circular fins and/or ribs assist in the ability of the plug to act as a barrier to keep the antimicrobial agent from entering the bloodstream. The deformable member may also be a polymer plug, tethered plug, or balloon plug. It may also be a combination of any of the above. Additionally, such a Device could load more antimicrobial due to its substantially increased surface area.

Figure 20:
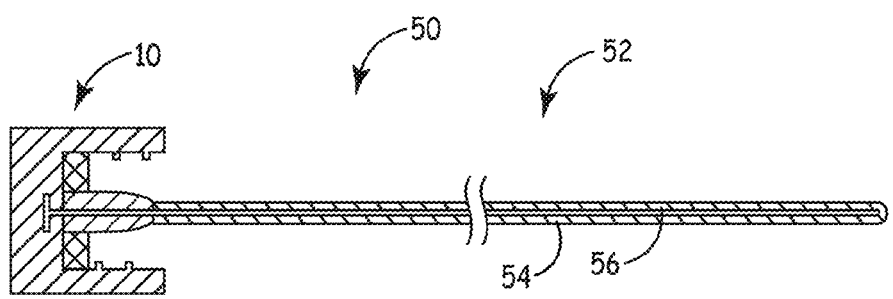
FIG. 20 is a cross-sectional view of a sponge plug, an alternative embodiment of the plug. The sponge plug is shown without the protective sheath and without the catheter.

In an alternative embodiment the deformable member may be a sponge or sponge plug that includes a porous material made from a compliant substance such as polyurethane sponge, silicone sponge, or other material. FIG. 20 shows the sponge plug 50 as an alternative embodiment to the hydrogel plug. The sponge plug 50 comprises the male Luer connector 10 and the sponge body assembly 52. The plug connector 10 is the same connector and has the same functions, as was described in the preferred embodiment. The sponge body assembly 52 comprises the sponge material 54, preferably made of polyurethane foam, and the sponge plug shaft 56, for example consisting of 0.012 inch diameter stainless steel. The purpose of the sponge material 54 is to conform to the lumen wall 103, 105 in a similar manner as the preferred embodiment shown in FIG. 7. The sponge material 54 is different than the preferred embodiment because the sponge material 54 has a larger diameter than the catheter lumens 102, 104 before it is inserted into the catheter 100 shown in FIG. 5. The sponge material 54 compresses and conforms to the catheter lumens 102, 104 when it is inserted into the catheter 100. The antimicrobial agent (not shown) may be incorporated into the sponge material 54 prior to insertion into the catheter 100. The sponge plug shaft 56 is designed to be flexible for going around curves, yet stiff enough to provide pushability.

The sponge plug 50 can use an open cell structure because the open cell structure has better compliance and can retain a larger amount of antimicrobial agent in comparison to a closed cell structure. The sponge design provides a large degree of compliance, thus maintaining contact with the catheter wall for removing biofilm. In one example, the sponge material extends along the entire length of the catheter, providing the maximum physical contact between the plug 50 and the catheter. An example embodiment of the sponge design has an internal shaft running along the length of the Device to provide greater pushability. Additionally, the sponge plug 50 may have an outer layer of abrasive fibers to aid in removing biofilm from the catheter wall. The fibers can be comprised of synthetic polyethylene terephthalate fibers orientated in an axial direction to allow expansion of the plug in the radial direction but to restrain expansion in the axial direction. The sponge plug 50 may also contain a dissolvable material, such as a salt or dissolvable antimicrobial agent, in order to keep the diameter of the plug smaller than the diameter of the catheter in order to minimize the risk of pushing infectious organisms out of the catheter. The dissolvable material preferably dissolves within one to ten minutes to allow the sponge plug to fully conform to the catheter's inner surface. The sponge plug 50 is removed by disengaging the connector at the catheter hub and pulling the plug 50 out of the catheter.

An alternative embodiment of the sponge plug 50 uses fine fibers in place of the sponge material in the deformable member. The fibers are compressed during manufacture in a manner that imparts axial strength to the plug. Alternatively, the fibers may be compressed around an axially stiff shaft. The axial strength is desirable to ensure that that plug can be fully inserted into the catheter lumen. The fibers may be made from a variety of materials such as, but not limited to, rayon, cotton, polyester, or polypropylene. Typically, the fibers have a diameter less than 20 microns.

Figure 21:
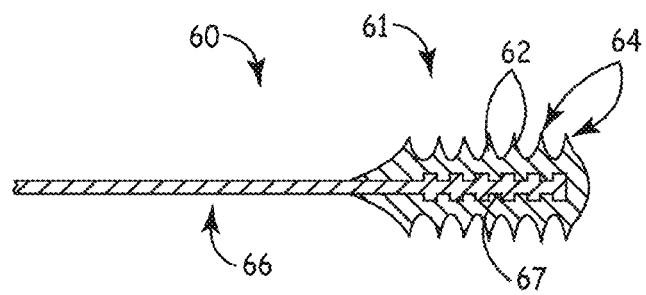
FIG. 21 is a cross-sectional view of the distal tip region of a polymer plug, an alternative embodiment of the plug.

A further alternative embodiment comprises a deformable member that is a plug with ribs that scrape along the length of the catheter. The plug may comprise polymer. FIG. 21 shows the distal tip region of the polymer plug 60. The polymer plug 60 comprises a connector (not shown, but it is optionally the same as or similar to the male Luer connector 10 in FIG. 1), a polymer plug shaft 66, and a polymer plug tip 61. The purpose of the polymer plug shaft 66 is to provide a means for pushing the polymer plug tip 61 into the catheter 100, shown in FIG. 5. The polymer plug shaft 66 must also be flexible to go around bends in the catheter 100. The polymer plug shaft 66 may be made of about 0.014 inch diameter stainless steel; however, other materials may be used, including metal or polymer materials. The end of the polymer plug shaft 66 ends at the corrugated end 67; the corrugation is designed to aid in attaching the polymer plug shaft 66 to the polymer plug tip 61. The polymer plug tip 61 is made with one or more ribs 62 molded from a highly flexible material, such as silicone. The ribs 62 are designed to flex and conform to the shape of the catheter lumens 103, 105. The rib tips 64 remain in contact with the catheter lumen walls 103, 105 in order to ensure that the antimicrobial agent remains confined from the body and body fluids.

The polymer plug 60 can be made from a compliant material, such as silicone or other compliant polymer. The polymer plug 60 optionally has a short tip 61, for example 5 millimeters long, that contacts the walls of the catheter. The plug region may be any length up to the entire length of the Device. In this embodiment, the remaining length of the plug Device can be formed of a flexible shaft or a flexible tether. The plug 60 is inserted into the catheter by pushing on the shaft or, in the case of the tether, by using hydraulic pressure from a syringe. The catheter is optionally filled with an antimicrobial agent while the plug is being inserted. Alternatively, the polymer plug 60 may run the entire length of the catheter, and the antimicrobial agent is applied along the outer surface of the plug, filling the space between the catheter wall and the plug.

Figure 22:
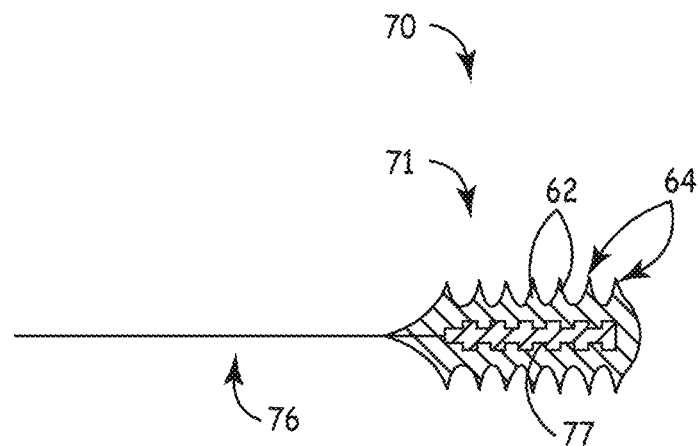
FIG. 22 is a cross-sectional view of the distal tip region of a tethered plug, an alternative embodiment of the plug.

A further embodiment is a tethered plug 70 configuration that is similar to the polymer plug with ribs that act to scrape the sides of the catheter wall. However, the tethered plug 70 is driven into the catheter using hydraulic pressure from a syringe rather than pushing it into position using a stiff shaft. In FIG. 22, the tether 76 attaches to the plug tip 71 to prevent it from becoming embolized. FIG. 22 shows the distal tip region of the tethered polymer plug 70. The ribs 62 and the rib tips 64 are identical to those of the polymer plug 60. The tether 76 is a strong flexible material, such as poly(tetrafluoroethylene) (PTFE), to ensure that the plug tip 71 does not embolize in the body. A narrowing at the distal end of the catheter can also be employed to prevent the plug tip 71 from becoming embolized. The tethered polymer plug 70 arrives in the dialysis center already loaded into a special syringe (not shown). The tethered plug 70 is preferably pre-loaded into a custom syringe to facilitate easy insertion into the catheter. The syringe is connected to the catheter connector 110 of FIG. 6, and the syringe plunger is advanced, causing the antimicrobial fluid inside the syringe to drive the tethered polymer plug 70 out of the syringe and through one of the catheter lumens 102, 104. The tethered plug 70 is designed to exit the catheter lumen 102, 104 by 1 to 4 millimeter, for example.

The travel of the tethered plug 70 is self-limiting because once it exits the catheter lumen 102, 104 (of FIG. 6, for example), the hydraulic pressure no longer acts on the tethered plug 70. The tether 76 is kept in tension by a friction applying member in the syringe (not shown). As the syringe reaches the end of its travel, the syringe activates a mechanism (not shown) that pulls on the tether, pulling the tethered plug tip 71 proximally by approximately 10 millimeters in order to seat the tethered plug 70 within the distal tip of the catheter lumen 102, 104.

The syringe may be designed to be detached from the syringe barrel, thus allowing the custom syringe tip to act as the plug connector. The tether 76 is securely crimped into a corrugated crimp sleeve 77. The corrugated crimp sleeve 77 is designed with a geometry to ensure good adhesion and physical entrapment within the tethered plug tip 71. A syringe may be used to withdraw the tethered plug 70 by aspirating with a syringe.

Figure 23:
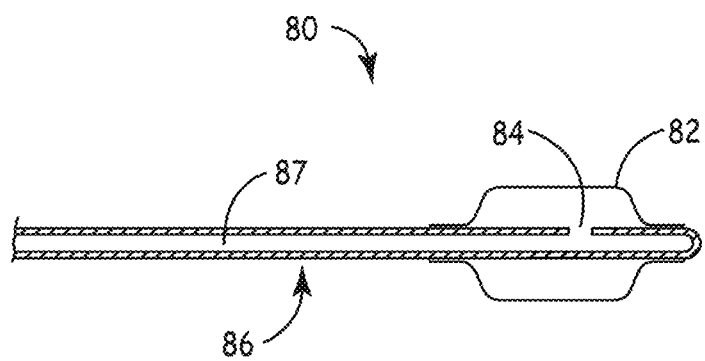
FIG. 23 is a cross-sectional view of the distal tip region of the balloon plug, an alternative embodiment of the plug.

An alternative embodiment comprises a balloon plug 80 design that includes a balloon 82, preferably at the distal tip of the plug, and a tubular shaft 86 that is used for inserting the plug and for providing a conduit for inflating the balloon. FIG. 23 shows the distal tip region of the balloon plug 80. The balloon plug 80 is very similar to the polymer plug 60 as shown in FIG. 21, except that the balloon plug 80 uses a balloon 82 instead of a polymer plug tip 61. The balloon 82 is inflated using fluid injected from a syringe, through the balloon shaft lumen 87, through the shaft hole 84, and into the balloon 82. The balloon 82 is preferably made of a flexible silicone, or other similar material, that will inflate and conform to the lumen walls 103, 105 of the catheter 100 shown in FIG. 5. The antimicrobial agent may be injected into the lumens 102, 104 prior to inflating the balloon 82 or, alternatively, the antimicrobial agent may be attached to the outer wall of the balloon shaft 86 such that the antimicrobial leaches out of the balloon shaft after the balloon is inflated.

After the plug is inserted such that the balloon 82 is positioned at the tip of the catheter, the balloon 82 is inflated, causing the balloon wall to conform to the wall of the catheter lumen. The remaining region of the catheter, proximal to the balloon 82, is filled with antimicrobial agent. The balloon 82 may be made from any of the numerous medical device balloon materials known in the art, such as semi-compliant polyethylene or compliant silicone. The balloon length is, for example, five millimeters long. Other materials may be used in balloon plug and various plug embodiments, such as polyurethane (such as Thermedics Tecophillic HP-60D-35 or Hydrogel TG-500), silicone, CELCON®, TECAFORM™ AH, MT (acetal copolymer), RADEL® R (polyphenylsulfone), UDEL® Polysulfone, ULTEM (polythermide), lot controlled UHMW, LENNITE® UHME-PE, TECANAT PC (USP Class VI polycarbonate rod), ZELUX® GS (gamma stabilized polycarbonate), acrylic (medical grade cast acrylic), TECAPRO™ MT (polypropylene heat stabilized), TECAPEEK CLASSIX™ (Prolonged to 30 day implantable Invibio® PEEK-CLASSIX™), TECANYL™, Polysulfone, PEEK®, PVDF (Meets USP Class VI), PROPYLUX®, medical grade PMMA, antimicrobial filled plastics, TEXO-LON™ Medical Grade PTFE (USP Class VI, FDA 21CFR177.1550), many other medical grade/FDA approved plastic products. In addition, metals may be incorporated into the plug design to add pushability to the shaft; materials include stainless steel (304, 304, 317, 17-4-ph, and others), titanium, and nickel titanium.

Radiopaque markers can be added to any of the plug types described herein for enhancing visualization with x-ray, fluoroscopy, or computer tomography. Radiopaque materials, along with the methods for incorporating them into medical devices, are well known in the art; some examples are gold, tantalum or platinum incorporated in their powder or solid form.

Other embodiments that deliver antimicrobial and/or antithrombotic agents, that confine and reduce the movement of infective organisms and fluids (blood, liquid antimicrobial agent and the like), and that scrub the walls of the lumen are anticipated. A plug with bristles orientated radially outward is one such example. The various embodiments may also be used in conjunction with one another. For example, the sponge plug may be combined with the hydrogel plug to produce the scrubbing action of the sponge with the swelling feature of the hydrogel.

While the invention has been particularly shown and described as referenced to the embodiments thereof, those skilled in the art will understand that the foregoing and other changes in form and detail may be made therein without departing from the spirit and scope of the invention.

What is claimed is:

1. An apparatus for delivery of an elongate member into the lumen of a trans-dermal catheter, the apparatus comprising:
   a protective sheath configured to at least substantially surround an elongate member and containing a shield coupler which is attached to a luer connector, the elongate member comprising a rod onto which an antimicrobial agent has been applied, and the elongate member secured to a connector insert; and
   a slidable member configured to travel along the protective sheath, the slidable member removably joined to the connector insert;
   wherein the elongate member is insertable into a lumen of a trans-dermal catheter by moving the slidable member and connector insert along at least a part of the length of the protective sheath such that the connector insert slides down the sheath to deliver the elongate member into the lumen of the trans-dermal catheter, and the connector insert attaches to the luer connector; and wherein the slidable member is further configured to detach from the connector insert upon attachment of the connector insert to the luer connector, such that the connector insert and luer connector become coupled to one another, and the shield coupler and luer connector are no longer joined to one another after the connector insert and luer connector are coupled.

2. The apparatus of claim 1, wherein the protective sheath has a slot along at least a portion of its length.

3. The apparatus of claim 2, wherein the slot comprises an opening along a portion of the length of the protective sheath.

4. The apparatus of claim 2, wherein the slot comprises a sealed portion configured to unseal upon contact with the slidable member.

5. The apparatus of claim 1, wherein the slidable member has an inner portion and an outer portion, such that the inner portion is positioned within the sheath and is in contact with the elongate member, and the outer portion is positioned outside of the sheath and is configured for grasping by a user.

6. The apparatus of claim 5, wherein the slidable member comprises an intermediate portion between the inner and outer portions, the intermediate portion configured to cut a path along the protective sheath.

7. The apparatus of claim 1, wherein the protective sheath and elongate member are substantially coaxial.

8. The apparatus of claim 1, wherein the elongate member can be delivered into a catheter without bending of the elongate member.

9. The apparatus of claim 1, further comprising a slidable member coupler releasably securing the slidable member and connector insert.

10. The apparatus of claim 9, further comprising a shield coupler secured to the protective sheath and releasably connected to the luer connector.

11. The apparatus of claim 10, wherein shield coupler is releasably connected to the luer connector by means of at least one tab projecting from the interior of the shield coupler into an opening in the luer connector.

12. The apparatus of claim 11, wherein the shield coupler is released from the luer connector by protrusions on the connector insert.

13. The apparatus of claim 1, luer connector secures the connector by protrusions on the connector insert.

14. The apparatus of claim 1, further comprising a grip secured to the sheath, the grip located opposite the luer connector.

15. The apparatus of claim 14, wherein the slidable member is configured to slide along the sheath between the grip and luer connector.

16. The apparatus of claim 1, wherein the luer connector is configured to screw onto the proximal end of the catheter.

17. An apparatus for delivery of an elongate member into the lumen of a trans-dermal catheter, the apparatus comprising:

a protective sheath configured to at least substantially surround an elongate member;

a slidable member configured to travel along the protective sheath, the slidable member operatively coupled to the elongate member and further connected to a connector insert; and a connecting member positioned on the distal end of the protective sheath, the connecting member configured to lock onto the proximal end of a trans-dermal catheter;

wherein the elongate member is insertable into the lumen of the trans-dermal catheter by moving the slidable member along at least a part of the length of the protective sheath such that the connector insert engages a luer connector such that the connector insert and luer connector become coupled to one another and the slidable member and protective sheath are released from the connector insert and luer connector.

18. The apparatus of claim 17, wherein the protective sheath has a slot along at least a portion of its length.

19. The apparatus of claim 17, wherein the slidable member has an inner portion and an outer portion, such that the inner portion is positioned within the sheath and is in contact with the connector insert, and the outer portion is positioned outside of the sheath and is configured for grasping by a user.

20. The apparatus of claim 17, wherein the connecting member comprises a male Luer connector.

21. An apparatus for delivery of an elongate member into the lumen of a trans-dermal catheter, the apparatus comprising:

a protective sheath configured to at least substantially surround an elongate member, the elongate member comprising a rod onto which an antimicrobial agent has been applied, the elongate member positioned co-axially within the protective sheath, and wherein a first end of the protective sheath is secured to a grip, and a second end of the protective sheath is secured to a shield coupler, the coupler releasably secured to a luer connector opposite the grip;

a slidable member configured to travel along the protective sheath, the slidable member operatively coupled to the connector insert, and the connector insert operatively coupled to the elongate member;

wherein the elongate member is insertable into a lumen of a trans-dermal catheter by moving the slidable member and connector insert along at least a part of the length of the protective sheath away from the grip until the connector insert is emplaced within the luer connector and the elongate member is emplaced within the proximal end of a transdermal catheter; and wherein the slidable member and connector insert become disengaged from one another after the connector insert is emplaced within the luer connector, and the shield coupler and luer connecter are no longer joined to one another after the connector insert and luer connector are coupled.

22. The apparatus of claim 21, wherein the protective sheath has a slot along at least a portion of its length.

23. The apparatus of claim 21, further comprising the luer connector positioned on the coupler at the second end of the protective sheath, the luer connector configured to lock onto the distal end of the trans-dermal catheter.

24. The apparatus of claim 23, wherein the Luer connector is configured to detach from the coupler at the second end of the protective sheath and remain locked on the trans-dermal catheter upon delivery of the elongate member into the lumen of the trans-dermal catheter.

* * * * *